United States Patent [19]
Antanavich et al.

[11] Patent Number: 6,165,225
[45] Date of Patent: Dec. 26, 2000

[54] RETRIEVABLE BIOARTIFICIAL IMPLANTS HAVING DIMENSIONS ALLOWING RAPID DIFFUSION OF OXYGEN AND RAPID BIOLOGICAL RESPONSE TO PHYSIOLOGICAL CHANGE, PROCESSES FOR THEIR MANUFACTURE, AND METHODS FOR THEIR USE

[75] Inventors: Richard D. Antanavich, Paso Robles; Randel Dorian, Orinda, both of Calif.

[73] Assignee: Islet Sheet Medical LLC, San Francisco, Calif.

[21] Appl. No.: 09/128,188

[22] Filed: Aug. 3, 1998

Related U.S. Application Data

[62] Division of application No. 08/542,506, Oct. 13, 1995, Pat. No. 5,855,613.

[51] Int. Cl.⁷ ............................................. A61F 2/02
[52] U.S. Cl. ............................................. 623/23.72
[58] Field of Search ................................. 424/422, 423, 424/424; 435/1, 177, 178, 179, 180, 182, 240.22, 240.241, 240.243; 623/1, 11, 12

[56] References Cited

U.S. PATENT DOCUMENTS

| | | |
|---|---|---|
| 3,093,831 | 6/1963 | Jordan . |
| 4,241,187 | 12/1980 | White . |
| 4,282,317 | 8/1981 | Roth . |
| 4,322,298 | 3/1982 | Persidsky . |
| 4,378,016 | 3/1983 | Loeb . |
| 4,391,909 | 7/1983 | Lim . |
| 4,402,694 | 9/1983 | Ash et al. . |
| 4,424,132 | 1/1984 | Iriguchi . |
| 4,686,098 | 8/1987 | Kopchick et al. . |
| 4,696,286 | 9/1987 | Cochrum . |
| 4,699,141 | 10/1987 | Lamberton et al. . |
| 4,892,538 | 1/1990 | Aebischer et al. . |
| 5,015,476 | 5/1991 | Cochrum et al. . |
| 5,106,627 | 4/1992 | Aebischer et al. . |
| 5,116,494 | 5/1992 | Chick et al. . |
| 5,141,581 | 8/1992 | Markham . |
| 5,156,844 | 10/1992 | Aebischer et al. . |
| 5,158,881 | 10/1992 | Aebischer et al. . |
| 5,182,111 | 1/1993 | Aebischer et al. . |
| 5,222,982 | 6/1993 | Ommaya . |
| 5,260,002 | 11/1993 | Wang . |
| 5,270,192 | 12/1993 | Li et al. . |
| 5,283,187 | 2/1994 | Aebischer et al. . |
| 5,284,761 | 2/1994 | Aebischer et al. . |

(List continued on next page.)

FOREIGN PATENT DOCUMENTS

| | | |
|---|---|---|
| 42 29 526 A1 | 3/1994 | Germany . |
| WO 93/24077 | 12/1993 | WIPO . |
| 95/18583 | 7/1995 | WIPO . |

OTHER PUBLICATIONS

Vox Sanquinis, vol. 68: 82–89, Feb. 1995, Boomgaard et al., Pooled Platelet Concentration Prepared by the.

Sambanis et al., Towards the development of a bioartificial pancreas: immunoisolation and NMR monitoring of mouse insulinomas, Cytotechnology (1994) 15(1–3): 351–363.

*Primary Examiner*—Michael J. Milano
*Attorney, Agent, or Firm*—David J. Brezner; Flehr Hohbach Test Albritton & Herbert LLP

[57] ABSTRACT

Bioartificial implants and methods for their manufacture and use are described, particularly bioartificial pancreases. In particular, the implants may be thin sheets which enclose cells, may be completely biocompatible over extended periods of time and may not induce fibrosis. The high-density-cell-containing thin sheets are preferably completely retrievable, and have dimensions allowing maintenance of optimal tissue viability through rapid diffusion of nutrients and oxygen and also allowing rapid changes in the secretion rate of insulin and/or other bioactive agents in response to changing physiology. Implantations of living cells, tissue, drugs, medicines and/or enzymes, contained in the bioartificial implants may be made to treat and/or prevent disease.

17 Claims, 4 Drawing Sheets

U.S. PATENT DOCUMENTS

| | | |
|---|---|---|
| 5,370,681 | 12/1994 | Herweck et al. |
| 5,380,526 | 1/1995 | Ise . |
| 5,385,582 | 1/1995 | Ommaya . |
| 5,387,237 | 2/1995 | Fournier et al. |
| 5,387,327 | 2/1995 | Kahn . |
| 5,429,821 | 7/1995 | Dorian et al. |
| 5,510,102 | 4/1996 | Cochrum . |
| 5,573,934 | 11/1996 | Hubbell et al. |
| 5,639,275 | 6/1997 | Baetge et al. |

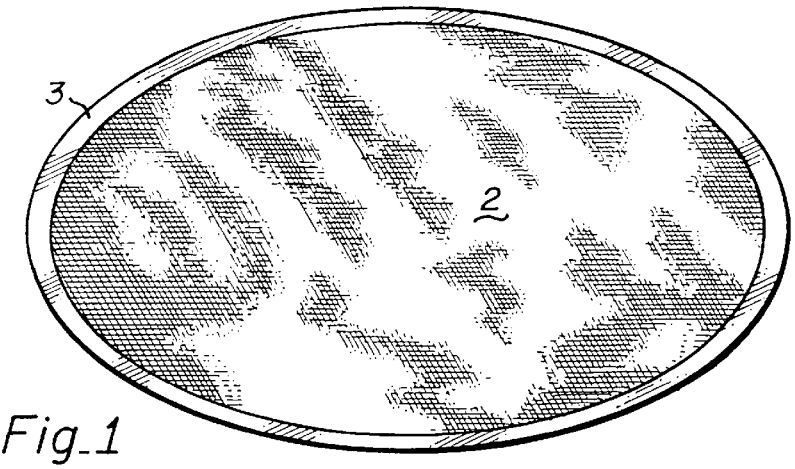
Fig_1
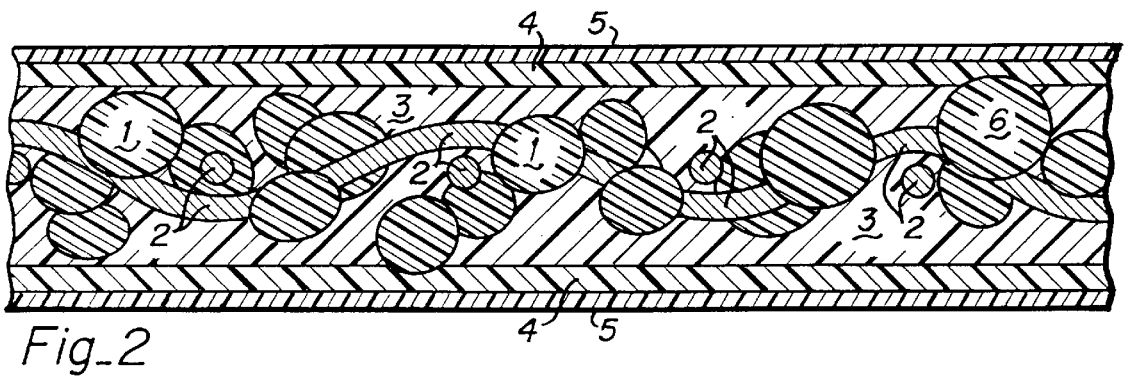
Fig_2
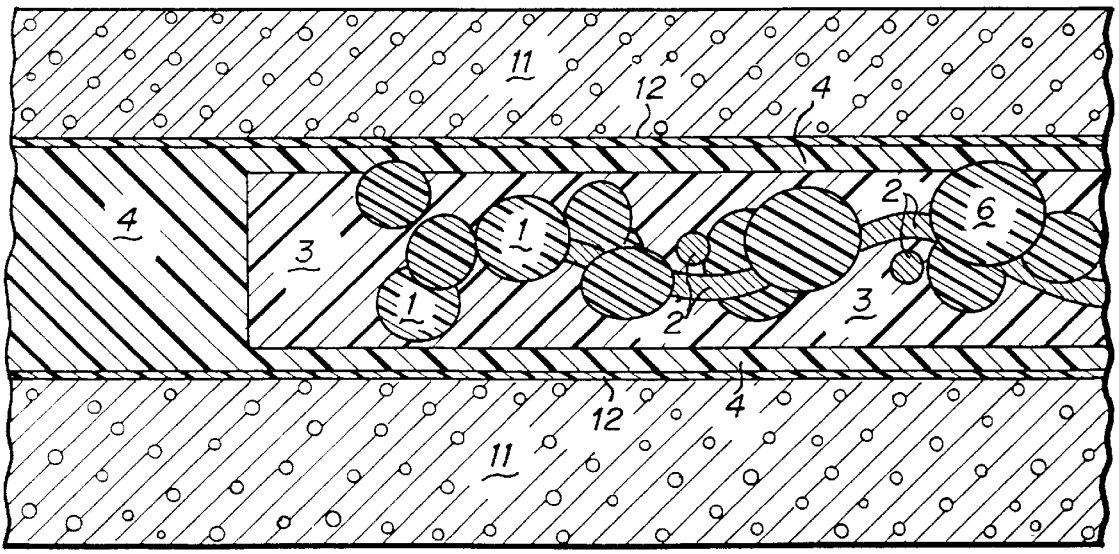
Fig_3

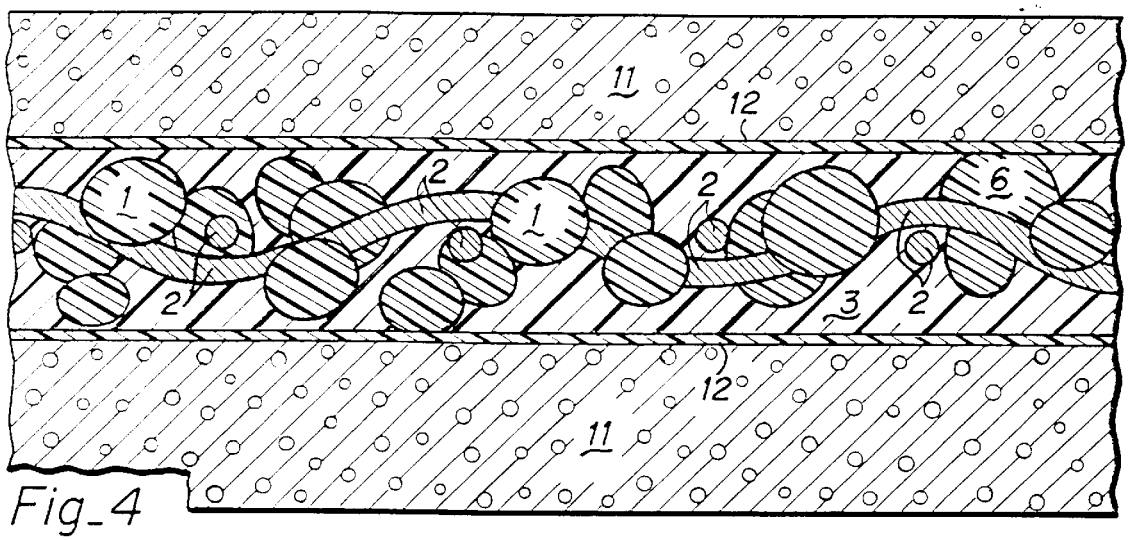
Fig_4
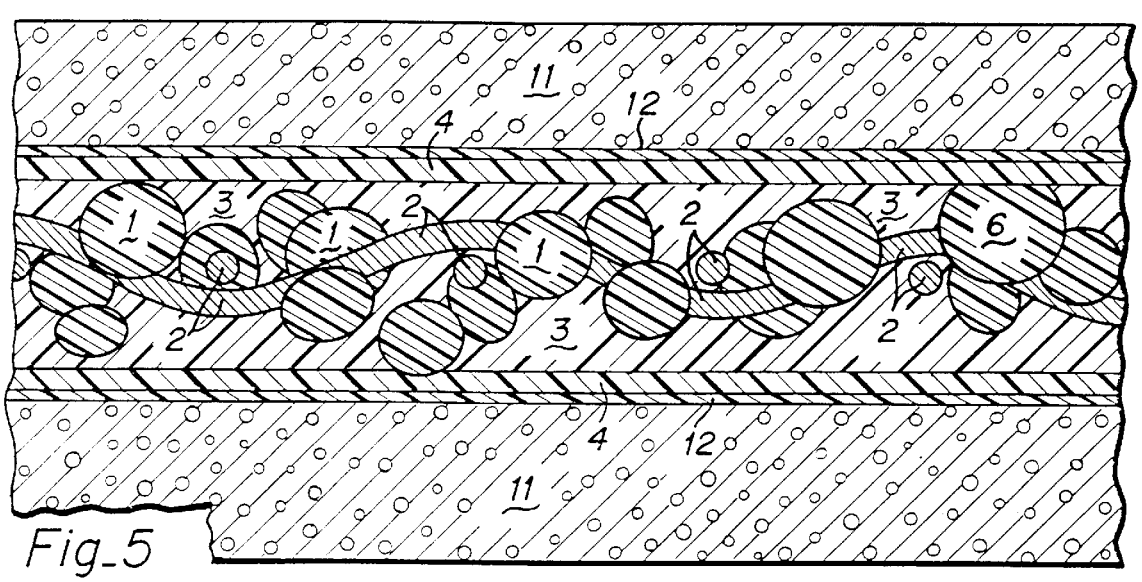
Fig_5
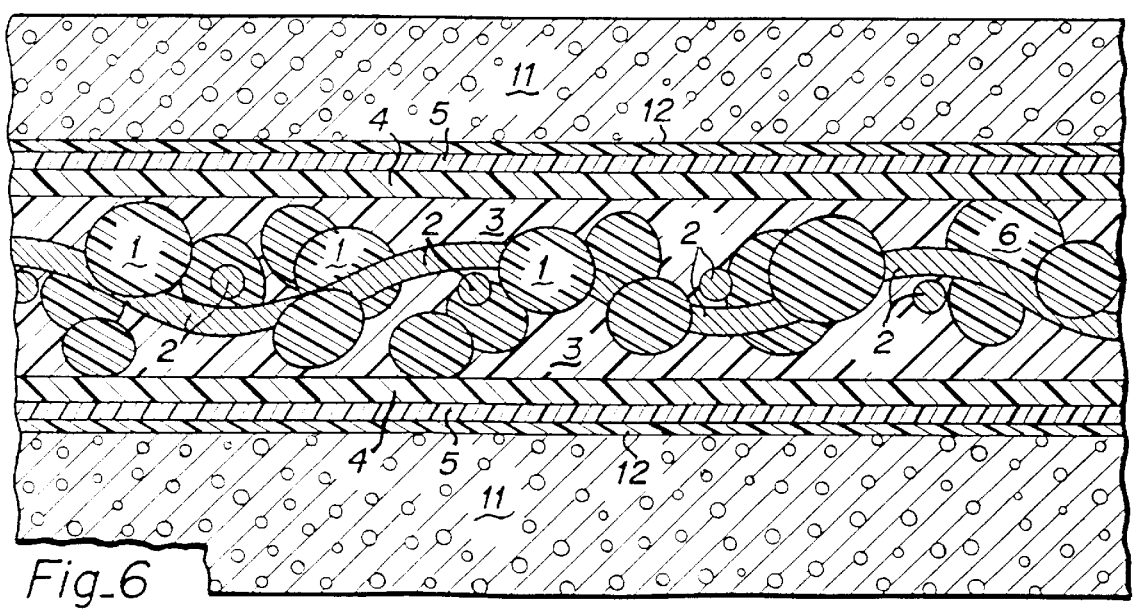
Fig_6

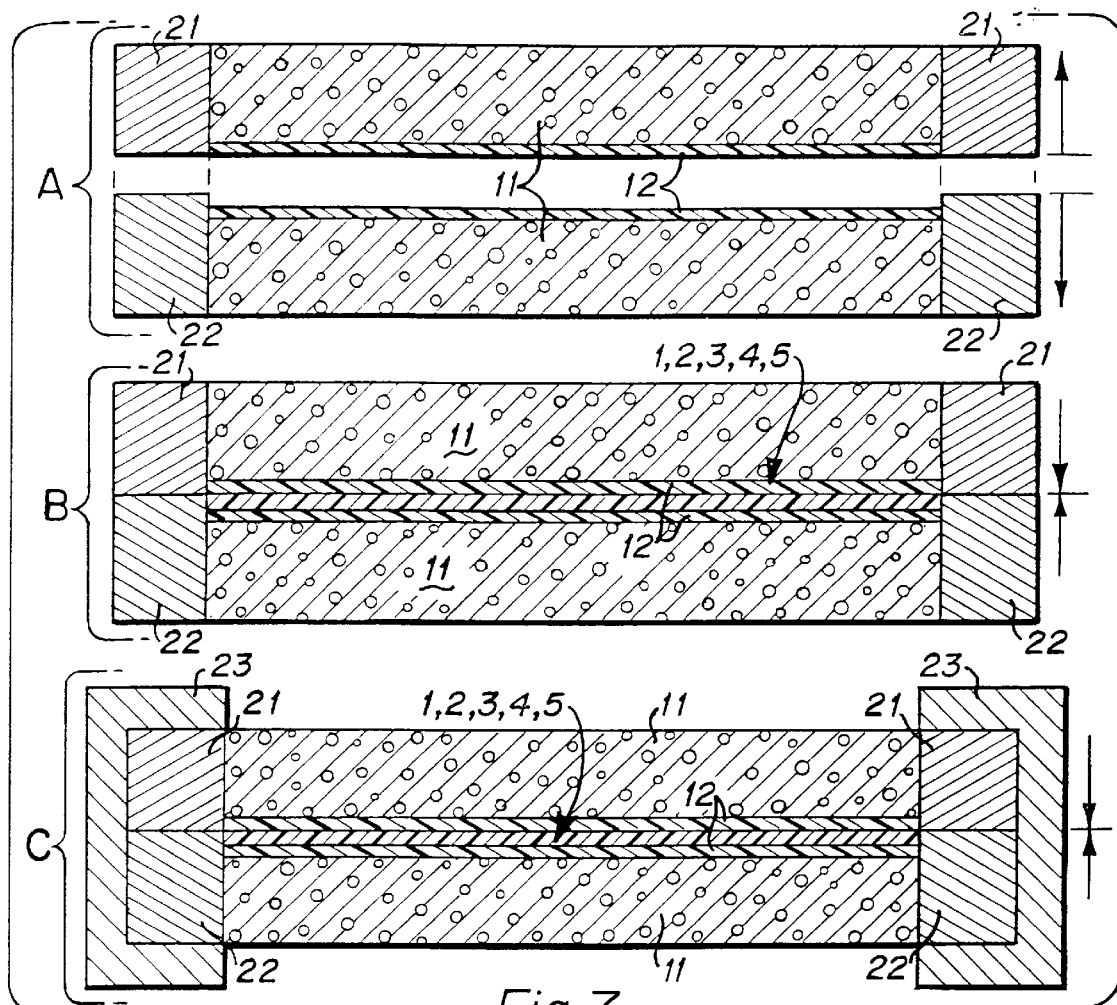
Fig_7
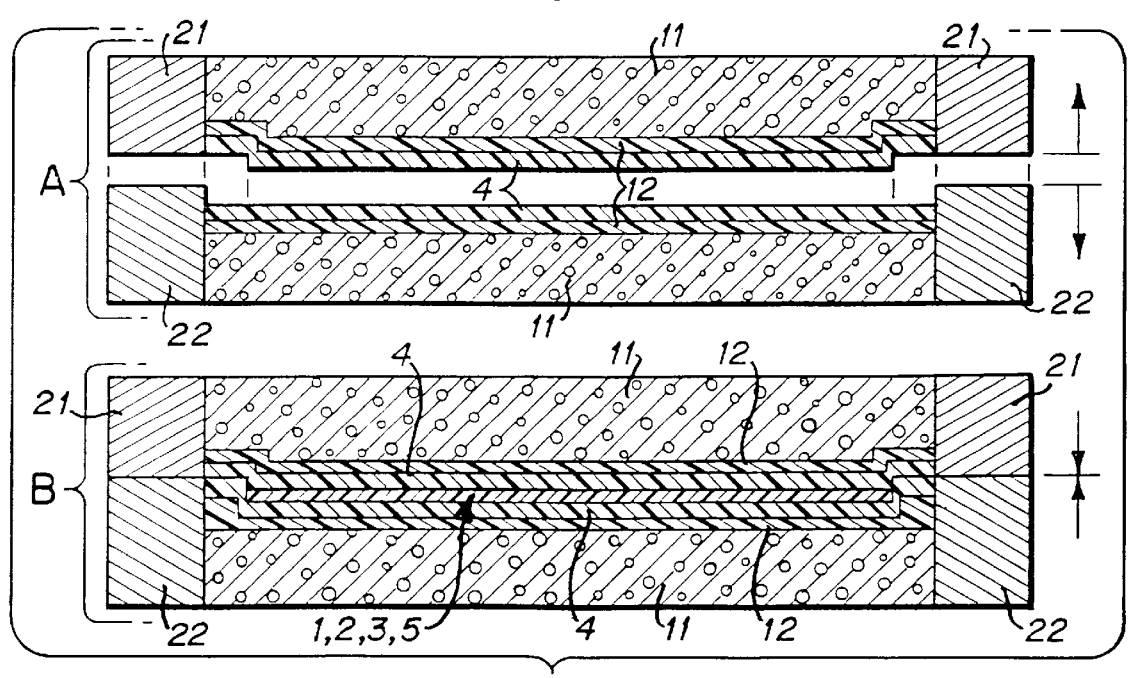
Fig_8

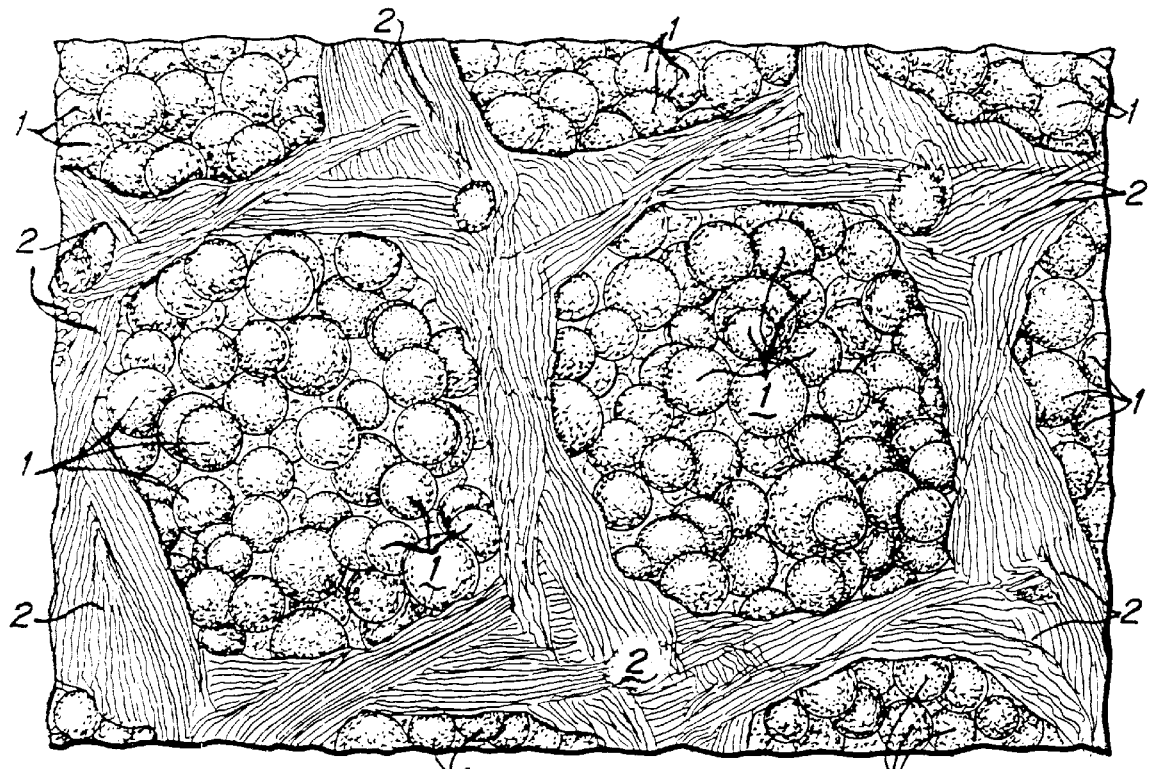
Fig_9
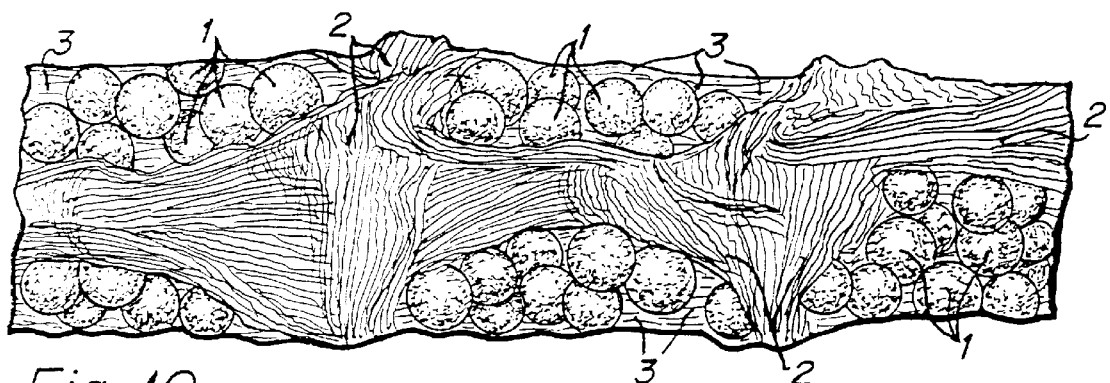
Fig_10
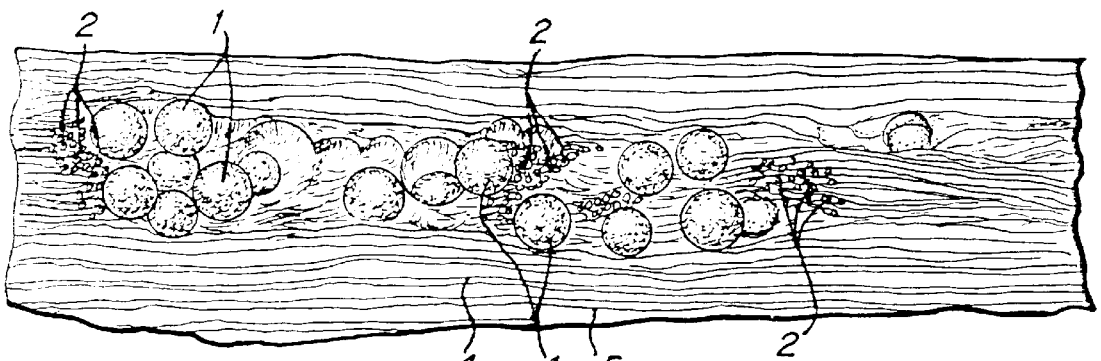
Fig_11

6,165,225

RETRIEVABLE BIOARTIFICIAL IMPLANTS HAVING DIMENSIONS ALLOWING RAPID DIFFUSION OF OXYGEN AND RAPID BIOLOGICAL RESPONSE TO PHYSIOLOGICAL CHANGE, PROCESSES FOR THEIR MANUFACTURE, AND METHODS FOR THEIR USE

This application is a division of 08/542,506 now U.S. Pat. No. 5,855,613 filed Oct. 13, 1995.

BACKGROUND OF THE INVENTION

1. Field of the Invention

The present invention is directed to the field of bioartificial pancreases, bioartificial implants generally, and methods for their manufacture and use. In particular, the present invention is directed to the fabrication of thin sheets which enclose cells, which are completely biocompatible over extended periods of time and which do not induce fibrosis. The present invention also concerns cell-containing thin sheets which are easily completely retrievable, and which have dimensions allowing maintenance of optimal tissue viability through rapid diffusion of nutrients and oxygen and also allowing rapid changes in the secretion rate of insulin and/or other bioactive agents in response to changing physiology. The present invention also concerns implantations made using these bioartificial implants. The present invention may be used for implantation of living cells, tissue, drugs, medicines and/or enzymes, contained in the bioartificial implants.

2. Discussion of the Background

Traditional medical treatments for functional deficiencies of biological organs have focused on replacing identified normal secreted products of the deficient organ with natural or synthetic pharmaceutical compositions. For example, for treating insulin-dependent diabetes mellitus (IDDM), also known as type I or juvenile diabetes, the normal secretion of insulin by the islets of Langerhans of the pancreas must be replaced since functional islets are no longer present in the pancreas. This islet function is emulated by administering insulin, titrating the injections in response to blood glucose level measurements. The normal production of hormone by the islets is poorly approximated. This therapy is known to be associated with premature morbidity and mortality.

Organ replacement has also been applied. For IDDM, whole pancreas and islet transplants both have been performed with significant success[1]. Such transplants require continuous use of immunosuppressive agents to prevent immunological rejection of the organ, depriving the patient of the full protective function of the immune system against disease and subjecting the patient to the side effects of the drugs.

The bioartificial implant is the manufactured solution to replacing organ function without reliance on immune suppression; this topic has been reviewed[2,3,4,5,6]. Many approaches have been tried for fabrication of bioartificial implants having in common the use of some semipermeable barrier allowing the tissue to function and simultaneously protecting tissue from rejection. Prior to the present invention, such bioartificial implants have proven unsatisfactory for a variety of reasons.

Because of severe limits on availability of human tissue, a practical therapy for IDDM will likely require the use of xenografts, most likely of porcine tissue. Porcine tissue is known to stimulate a vigorous immune response in humans, including complement mediated rejection of the xenograft, posing a significant obstacle to use of porcine tissue in a bioartificial implant. The bioartificial implant barrier should sufficiently exclude antibody-complement to prevent complement mediated Damage to cell and tissue xenocrafts.

Some bioartificial implants require grafting into the vascular system, usually with connections to an artery and a vein to take advantage of the pressure difference. Blood flow through such vascular grafts has proven to be traumatic to blood, and continuous systemic administration of pharmaceutical preparations to prevent clotting and foreign body reactions is required. Thus optimal bioartificial implant design, not requiring continuous systemic pharmaceutical administration, is limited to implants that rely on passive diffusion.

Most such passive diffusion bioartificial implants fail because their dimensions are such that the enclosed tissues cannot receive enough nutrients, especially oxygen. When tissue is starved of oxygen its metabolism declines and it loses its ability to secrete hormone. Extended hypoxia leads to cell death.

In these same devices, the tissue may be prevented from responding in a timely way to changes in the physiological environment because of the dimensions of the bioartificial implant. In the case of implants containing insulin-producing islets, an unsatisfactory bioartificial implant may not be able to sense that previously secreted insulin has successfully reduced blood sugar levels, and thus, will continue to secrete insulin even when the effect of this insulin is to plunge blood sugar levels below normal, endangering the host.

Many bioartificial implants fail because their surface is not biocompatible. When exposed to living tissues, especially when they have been seeded with allogeneic or xenogeneic living tissue, they provoke a foreign body response. The foreign body response may be caused by a material on the surface of the implant, antigens shed by the cells within, or by a combination of both. The foreign body response includes fibrosis, in which fibroblasts and macrophages apply proteins including collagen to the surface of the implant, attracting other effector cells, and eventually leading to the formation of a capsule of connective tissue that isolates and starves the implant.

Some bioartificial implants are unsatisfactory because they cannot be easily removed in the event of implant failure or dysfunction.

Some processes previously developed for fabrication of bioartificial implants did not yield reproducible products having the desired porosity and thickness required for the implant.

Some processes previously developed did not completely cover the living tissue, thus allowing access by host immune system to the living tissue, leading to foreign body reactions and/or sensitization and antibody formation followed by complement-mediated lysis.

Some processes previously developed for bioartificial pancreas implants did not make efficient use of islets, wasting a significant fraction of them during fabrication.

Some bioartificial implants are so bulky that implantation is difficult or impossible. This problem occurs when only a small fraction of the volume of the implant consists of living cells.

Prior to the present invention, all bioartificial implants have proven unsatisfactory for one or more of these reasons, and for other reasons as well.

EASE OF COMPLETE RETRIEVAL

The need for complete retrieval of the bioartificial implant in the event of failure has been stressed by several workers in the field[7,8,9], especially Paul Lacy, a recognized leader in islet implant research. He has criticized encapsulated islets[9]:

"To be feasible for broad use, the capsules would have to be smaller and more stable. In addition, investigators would have to develop a way to retrieve all the capsules readily in the event removal became necessary."

Another reason that the optimal bioartificial implant must be easily completely retrievable is that such devices will require review by the FDA's division of biologics before sales in the United States[10]. Such review examines all safety issues and risks, including ease of retieval in the event removal becomes necessary. A clinical trial of a bioartificial implant in the United States was done under an FDA approved protocol[11].

DIFFUSION AND BIOARTIFICIAL IMPLANT DIMENSIONS

It is now widely recognized that a successful bioartificial implant must have dimensions that permit efficient diffusion of nutrients into the implant and secretion of bioactive agents out of the implant. Yet the vast majority of bioartificial implants described in the literature have dimensions which make efficient diffusion impossible, either because they were manufactured before the magnitude of the requirement was understood, or because there was no art to manufacture the implant with the required dimensions.

Theoretical studies have predicted the maximum dimensions permissible based on the physics of diffusion. The maximum dimension is a function of the density of tissue in the implant. Experimental studies confirm the theoretical limits to passive diffusion and point to the parameters of implant dimension.

Diffusion both into and out of the bioartificial implant must be considered. Secreted products must diffuse out of the bioartificial implant efficiently. Nutrients must diffuse in at a rate sufficient to support normal cellular metabolism. The rate-limiting nutrient is oxygen, and implants that die from lack of nutrients usually die of hypoxia.

First, in an islet bioartificial implant, insulin must diffuse quickly out of the device in response to changes in ambient glucose levels. Implants that are too large delay insulin response. For instance, after glucose stimulus is removed, hollow fiber implants (730 $\mu$m O.D.) continue to secrete insulin long after glucose has normalized[12]. This excess insulin can result in potentially life-threatening low blood sugar.

Experimental studies have shown that bioartificial implants that are larger than 350 $\mu$m in their shortest dimension significantly delay the release of insulin in response to glucose challenge[13,14]. Although studies of insulin release kinetics in vitro alone are useful, glucose tolerance and insulin levels should be measured in vivo in an animal model to more conclusively determine the potential effectiveness of a particular implant structure and design.

Second, the most difficult problem associated with implants relying on passive diffusion is oxygen diffusion. The importance of oxygen diffusion has only been recognized relatively recently. Current theoretical models predict that oxygen diffuses to a depth of less than 200 $\mu$m through living tissue[5,15]. The most detailed analysis of the relationship between implant dimensions, implant shape, engraftment, oxygen tension and islet viability has been published recently by Colton[5]:

Maintenance of maximum cell viability and function is essential and, in the absence of immune rejection, is limited by the supply of nutrients and oxygen, especially the latter . . . The oxygen levels to which the islet cells are exposed are important from two standpoints, viability and function . . . Planar diffusion chambers, preferably with high tissue density, represent an attractive configuration for immunoisolation devices. Diffusion chambers prepared with parallel, flat sheet microporous membranes were employed extensively several decades ago in early studies of immune rejection during transplantation. Invariably, the membranes employed produced an extensive fibrotic foreign body response composed of an avascular layer of fibroblasts in a collagen matrix which restricted the supply of oxygen and nutrients, resulting in minimal survival of the encapsulated tissue . . . Only when the oxygen source is brought to within about 25 $\mu$m from the surface of the transplanted tissue does the $pO_2$ at the center of a 100 $\mu$m-thick slab stay above zero.

This analysis shows that diffusion of oxygen is crucial for islet viability and function and that the shortest dimension of the coating, capsule or slab/sheet permitting oxygen diffusion throughout the structure ranges up from 100 $\mu$m depending on tissue density, implant configuration and the proximity of oxygenated tissue.

Studies of islets in hollow fibers, microcapsules and coatings have supported these theoretical conclusions[14,16,17,18]. NMR/EPR studies of $O_2$ concentration suggest that oxygen is low in alginate capsules[19]. These observations confirm that the configuration of the device must be very thin. As a rule of thumb, each cell must be less than 200 $\mu$m from the surface of the bioartificial implant to receive oxygen, assuming that the implant is in contact with well oxygenated tissue.

BIOCOMPATIBLE MATERIALS

There is considerable confusion about the term "biocompatibility." The sciences concerned with implantable medical devices use the term very differently from the sciences concerned with implants. For a device, biocompatibility means that the material induces engraftment, e.g., the vascular graft is covered with a layer of collagen fibers. This permits overgrowth of endothelial cells, which is desirable for a vascular graft. In contrast, such overgrowth will starve a cellular implant. Thus, biocompatibility for a living implant means the material will not promote cellular adhesion. The term "biocompatible" is used here to mean that the material by itself or in combination with living tissues does not produce foreign body reaction or fibrosis.

Surprisingly few materials meet this definition. It is generally believed that the foreign body reaction is initiated when proteins adhere to the foreign body[20]. Thus the material, to prevent the initial step of protein adsorption, should be very hydrophilic. For example, almost every biocompatible polymer is a polysaccharide, a polyalcohol, an organic acid, or a combination thereof.

Most published work makes use of alginate, a polymer of alginic acids, which are sugar acids. Other biomaterials that are claimed to be biocompatible include agarose[21], agarose/poly(styrene sulfonic acid)[22], hydroxyethyl methacrylate-methyl methacrylate copolymer[23], polyvinyl alcohol[24,25], protamine-heparin[26] and others. One group has photopolymerized a skin of polyethylene glycol onto alginate to improve its biocompatibility[20]; another used free radical polymerization of ethylene oxide and alginate to improve stability[27].

The most commonly used material for fabrication of bioartificial implants has been alginate, usually in combination with a polycation such as poly-L-lysine to form a membrane. The original alginate/polylysine capsule was shown to ameliorate diabetes in mice over fifteen years ago[28].

This occurrence of alginate in nature is mainly in the marine brown algae (Phaeophyta), soil bacteria and Pseudomonas. Alginate is a family of unbranched co-polymers of (1–4)-linked β-D-mannuronic acid (M) and α-L-guluronic acid (G). It is located in the intercellular algae matrix as a gel containing cations (predominantly $Ca^{2+}$) that crosslink the polymer fibers. Alginates appear to be block co-polymers comprised of homopolymeric blocks of M and G with regions of alternating MG. Methods have been developed for purification of high M and high G fractions of various molecular weights[29,30,31,32] sufficiently pure to make them biocompatible[33,34,35,36].

Alginates obtained from marine algae comprise approximately 40% of the dry weight of the kelp. Because of its ability to retain water and its gelling, viscosifying and stabilizing properties, alginate is widely used industrially.

Until recently, alginate/polylysine capsules induced fibrosis and were not biocompatible[3]. Grafts failed over periods of days ant months. Such grafts were found to be covered with dense fibrous overgrowth.

These capsules caused fibrosis for several possible reasons. First, polylysine is fibrogenic. Capsules made with alginate alone are less fibrogenic[37]. In addition, researchers at the University of Gießen and the University of Würzburg[36,35], and separately at the University of California[33,34,29], succeeded in showing that alginate fibrosis was caused by impurities in alginate. Sufficiently purified alginate does not induce fibrosis. (The concept proposed by University of Trondheim that high-gulurcnate alglnates are biocompatible while high-mannuronate are not[38] has been shown to be incorrect[37,39].) Thus, alginate can be made biocompatible (as defined above) with a series of rigorous purification steps.

One of the present inventors (Dorian) in collaboration with researchers at the University of California established that removal of sufficient contaminants from alginates results in alginate fractions that are nonfibrogenic, regardless of the G, M and GM content[33,34]. It was also shown that the molecular weight and block contents can be manipulated to produce alginates with desirable physical properties. Thus, it is now possible to produce both high M and high G alginates that are biocompatible with and without cells or islets.

Finally, it is worth noting that some workers in the field have concluded that biocompatibility, as we have defined it, is not necessary for a successful implant. Instead of a material that is ignored by the body's foreign body reaction cells, they seek one that produces a certain type of foreign body reaction[2]:

Biocompatibility is most often achieved by a careful manipulation of composition, purity, geometry, handling, surface morphology, and surgical techniques to yield an implant and implant site which is sufficiently inoffensive to the host to remain below the threshold of stimulation required to provoke macrophage activation and fibroblast deposition . . . Less frequently but also successfully, biocompatibility can be obtained by texturing the surface of the implant to encourage the growth of a host vascular network at the implant surface . . . This strategy no longer requires membrane and materials which do not engender a foreign body response and consequently permits somewhat greater latitude in setting membrane transport requirements . . .

This approach has been tried in the past without success, and was patented[40].

We reject this approach because we believe that strict neutrality is desirable. For us, "biocompatible" means that the material by itself or in combination with living tissues does not produce foreign body reaction or fibrosis.

AUTO INHIBITION OF PRODUCT SECRETION

Pancreatic islet cells in vivo receive arterial blood, and therefore, sense the same levels of nutrients and hormones in the blood prevalent elsewhere in the body. Islet cells in a bioartiftcial implant may experience higher levels of their own secreted hormones because they are dependent on diffusion to disperse hormones. A bioartificial implant which inhibits or impedes diffusion of hormones will cause islet cells to respond to an artificially high concentration of hormones. For example, secretion of insulin by islets is inhibited by high ambient levels of insulin[41]. It may be advantageous to make the implant as thin as possible and thus aid the diffusion process.

COMPLEMENT-ANTIBODY LYSIS OF IMPLANTS

As described previously, passive diffusion of nutrients, oxygen and secretory products such as insulin (M.W.=7 kD) should be uninhibited to maximize the effectiveness of a bioartificial implant. This suggests that the membrane or coat of the bioartificial implant should have large pores. Larger pores, however, would admit antibodies (M.W.=160 kD), and larger, If sufficiently, complement (M.W. [Clq]= 390 kD). If antibody and complement can penetrate the coat or membrane, the cells inside the implant are at risk of lysis and death.

Microcapsules have been made that inhibit antibody and complement diffusion sufficient to prevent islet lysis and permit normalization of blood sugar in mice. This was shown even when immune sensitization was demonstrated using MLC cultures[36]. However, similar results in higher mammals have not been reported.

The complement system, which exists in its most active ("complete") form only in higher mammals, is triggered by antibody and can kill foreign tissue in minutes[42]. Normally, allografts unprotected by bioartificial barriers are killed by cellular attack, not complement attack. However, xenografts often trigger a vigorous antibody and complement response. In some donor-recipient combinations (e.g., pig-to-dog), preformed antibodies exist and the complement response occurs minutes after implantation, before sensitization can occur.

The vast majority of islet implant studies have been performed using inbred mouse strains as recipients. These animals are deficient at mounting a complement mediated response, and such studies are thus not predictive of, for example, a human response to xenografts[43].

Because of ethical concerns and a shortage of suitable human tissue, one practical therapy for human diabetes is a xenograft bioartificial implant. Recent studies, however, have demonstrated that porcine-to-monkey xenografts can trigger a vigorous antibody and complement response, raising grave concerns for porcine-to-human xenografts[44].

The optimal bioartificial implant should prevent diffusion of antibody and complement sufficiently well to prevent antibody and complement lysis of the living cells within the bioartificial implant. Microporous membranes by their nature do not have a sharp molecular weight cutoff. Rather, the membranes increasingly inhibit diffusion as molecular weight increases, in a manner represented by a sigmoid curve[5]. Thus, free diffusion of insulin and sufficient inhibition of complement diffusion require a subtle and complex "tuning" of the membrane. Experimental demonstration of this phenomenon caused the Gießen group to comment[45]:

"Our results lead to the concept of persistent immune interaction after 'immunoisolated' transplantation. In this case a bioartificial pancreas could not be described as an immunoisolated islet transplantation but as an 'artificially immunoprivileged site of transplantation.'"

In conclusion, the concept of immunoisolation should be supplanted by a recognition that the ideal implant is a subtle balance of multiple demands, including the molecular weight diffusion function of the membrane or coat, in one strategy to fabricate a successful bioartificial implant.

INEFFICIENT, INCOMPLETE AND INCONSISTENT FABRICATION METHODS

Islets are precious. A loss of fifty percent of the islets during fabrication of the bioartificial implant would mean only half as many people with IDDM could be implanted. Some technologies are known to have a poor yield. For instance, air knife coating has a yield of 70%[46], and barium alginate density gradient coating has a yield of 40%[47]. Most published methods do not report the yield, or survival rate, of islets.

Another form of inefficiency is a device design that includes too much "dead" space (i.e., space unoccupied by tissue or cells). Hollow fiber and disc designs have been reported to be 97% "dead" space[9] and 96% "dead" space[14], respectively. In these configurations, the ratio of the dead space to the islet volume is $\geq 25$. In the optimal bioartificial implant, this ratio should be much smaller. In the limiting case, the implant would be pure tissue.

As a result of imperfect coating, it is possible that islets may protrude from finished capsules, leading to fibrosis[48]. Another consequence of imperfect coating can be sensitization followed by antibody production, leading to complement lysis.

Defects in the capsules have been reported to lead to fibrotic overgrowth[49]. Some methods do not appear to be reproducible[50].

The optimal bioartificial implant fabrication method should be reproducible and have a high yield. The optimal bioartificial implant should have a small volume ratio and no cells protruding, and be free of physical imperfections that lead to fibrosis.

CELLULAR TROPHIC FACTORS

The optimal bioartificial implant favors the health of the implanted cells. For instance, good glycemia helps all islet implants. It has been demonstrated that islets retain more of their original mass following implantation when the glycemic level of the host is maintained near normal as the islets are engrafting[51]. It is therefore not surprising that clinical researchers report greater success when efforts were taken to stabilize islet implant recipients' blood sugar levels[52].

A number of reports suggest methods to improve islet cell mass, viability and functionality by including substances in the bioartificial implant composition. Given the importance of oxygen in maintaining cell viability, it is not surprising that there is a report that hemoglobin improves oxygen transport and thus isle: viability[18]. Collagen also has a reported benefit to islet viability, presumably because islets are attachment-dependent cells[7]. Other components of the extracellular matrix including fibronectin, laminin, and tenascin are also recognized as playing a role in cell growth and differentiation[53], and thus may be sustaining.

Numerous trophic hormones and factors have appeared in the literature, including such trophic factors as insulin-like growth factor-I, insulin-like growth factor-II, transforming growth factor-alpha, hepatocyte growth factor/scatter factor, platelet-derived growth factor, and ilotropin, a paracrine/autocrine factor associated with islet differentiation.[54,52] There is a report that antioxidant vitamins reduce fibrotic overgrowth[55], and another that the vitamin nicotinamide helps islet viability[56].

Another approach to maintaining cell viability and functionality is to co-culture with cells that secrete trophic factors[57].

The cotimal bioartificial implant may include all such substances to the extent that they are compatible with other components and are beneficial to the implanted cells.

USEFUL CELLS FOR INCORPORATION IN BIOARTIFICIAL IMPLANTS

Although the discussion herein focuses on islets of Langerhans for treatment of diabetes, many uses of cellular implants to treat diseases have been proposed, including treatment of hemophilia, dwarfism, anemia, kidney failure, anemia, chronic pain, Alzheimer's disease, fulminant hepatic failure, Parkinson's disease, etc. This topic has been reviewed[58].

PREVIOUS APPROACHES

Numerous bioartificial implants have been described. The following discussion is limited to passive diffusion type implants each containing multiple islets, and does not include individually encapsulated islets or vascular devices. (Two examples of capsules are included in the table for purposes of comparison.) In many cases dimensions and tissue density are not reported in the reference, and we have noted the assumptions used to generate numbers in the summary table at the end of the section. Oxygen at the center of the implant has been measured very rare y; oxygen levels were determined by applying the analysis of Colton at al.[5]

General reviews of immunoisolation technologies were noted earlier; discussions of planar congifurations—slabs, discs and sheets—have also been published. For the most comprehensive and detailed on older research, see Scharp[59], and for the most 10 recent work, see the two reviews by Colton[4,5].

Aebischer et al.[60] have described a tubular polymer implant made by "coextruding an aqueous cell suspension and a polymeric solution through a common port to form a tubular extrudate having a polymeric outer coating which encapsulates the cell suspension." In one embodiment, the tubular extrudate is sealed at intervals to define separate compartments connected by polymeric links. This system has a low cell density, reported at 0.1% in the patent example. The dimensions of the cylinder device do not permit oxygen to reach the center.

Andersson et al.[61] describe a laminated double membrane disc designed to simultaneously prevent cellular invasion and promote vascularization. The paper describes fibroblast invasion suggesting a lack of biocompatibility. While tissue density is high and the thickness is sufficiently small to permit oxygen throughout the device, the small diameter of the disc results in insufficient volume per transplant. The design does not appear to permit sufficient control over thickness if the diameter is larger.

Ash et al.[62] have described a system comprising a bundle of fibers that remains under the skin allowing replacement of cells. The dimensions of the sack-like device do not permit oxygen to reach the center if cell density is greater than 10%.

Aung et al.[24] have described a biohybrid artificial pancreas utilizing mesh-reinforced polyvinyl alcohol hydrogel tubes as membranes. The tubes have a 2 mm ID, and the membrane is 200 $\mu$m thick. The configuration prevents suitable kinetics and oxygen tension. As Aung's group reported[63], ". . . islets tend to aggregate into large clumps, and subsequent central necrosis occurs, probably due to the hypoxia of the central portion, resulting in impairment or loss of function of the islets within 1 to 2 weeks."

Thus, experimental results confirm that the thickness of the tube produces anoxia at the center.

Bae et al.[64] describe an implantable and refillable biohybrid artificial pancreas. The configuration is a disc shaped pouch. The polymer (a cellulose acetate coated membrane) is not biocompatible. The dimensions of the disc device do not permit oxygen to reach the center if cell density is greater than 10%.

In a study that measured oxygen tensions in an acrylic tube implant, Bodziony[16] found that the amount of oxygen present is too low to support viability of islets. The amount of oxygen present was calculated to be depleted by islet metabolism in less than three minutes.

Gaskill[65] proposed a passive diffusion "intravascular artificial organ comprised of a flexible, hollow, semipermeable catheter containing living cells or tissue." It is now known that the proposed materials induce thrombosis when placed in flowing blood. Although dimensions are not disclosed, a tube with sufficiently small diameter to permit oxygen diffusion to the center would be several meters long, much longer than one shown in FIG. 1 of the patent. Thus the invention of Gaskill does not have dimentions allowing oxygen to reach the center if cell density is greater than 10%.

Inoue et al.[25] constructed a tube of polyvinyl alcohol membrane. The dimensions of the cylinder device do not permit oxygen to reach the center if cell density is greater than 10%.

Jordan[66] describes a sack/tube, and even says that "the length of the shortest diffusion path between the interior side of the container wall and the center of the glandular tissue must not be longer on the average than two millimeters." However this length is not correct based on current understanaing of oxygen diffusion through tissue, and it is also incorrect to neglect the effects of diffusion through the container wall. The Jordan design would have no oxygen in its center if cell density is greater than 10% due to its dimensions.

Kopchick et al.[67] use hollow fibers seeded with genetically engineered cells to deliver bovine growth hormone. The dimensions of the cylinder device do not permit oxygen to reach the center if cell density is greater than 10%.

Lacy et al.[8] studied hollow fibers fabricated from an acrylic copolymer encapsulating small numbers of rat islets immobilized in an alginate hydrogel. The dimensions of the cylinder device do not permit oxygen to reach the center if cell density is greater than 10%.

Lanza et al.[68] used Amicon XM-50 membrane tubes sealed at the ends. The dimensions of the cylinder device do not permit oxygen to reach the center if cell density is greater than 10%.

Laue et al.[54] studied a regenerated cellulose hollow fiber system. The dimensions of the cylinder device do not permit oxygen to reach the center if cell density is greater than 10%.

Loeb[69] describes an "artificial endocrine gland for supplying a hormone to a patient including an implantable housing placed in the body and having an impermeable extracorpeal segment and a semipermeable subcutaneous segment [with a] replaceable envelope containing live hormone-producing cells such as pancreatic islet cells." Although dimensions are not disclosed, a tube with sufficiently small diameter to permit oxygen diffusion to the center would be many meters long, much longer than one shown in FIG. 8 of the patent. Thus the invention of Loeb does not have dimentions allowing oxygen to reach the center if cell density is greater than 10%.

Ohgawara et al.[55] describe a diffusion chamber, but dimensions are not given. A cell density of 2% is described.

Penfornis et al.[70] also made use of the Amicon XM50 hollow fiber described by Lanza. The dimensions of the cylinder device do not permit oxygen to reach the center if cell density is greater than 10%.

Scharp et al.[11] studied hollow fibers fabricated from an acrylic copolymer. Human islets were macroencapsulated and allotransplanted subcutaneously. Recipients were patients with type I or type II diabetes and normal control subjects; none was immunosuppressed. The dimensions of the cylinder device do not permit oxygen to reach the center if cell density is greater than 10%.

Scharp has also developed planar diffusion chambers which have been described by others (see table).

Schrezenmeir et al.[18] used regenerated cellulose capillary membranes. The principal object of the study was to show that hemoglobin helped maintain viability by conducting oxygen. The dimensions of the cylinder device do not permit oxygen to reach the center if cell density is greater than 10% in spite of the hemoglobin.

Tze et al.[71] investigated polysulfone fibers in a coil configuration, and found massive fibrosis in only a few days. The dimensions of the device do not permit oxygen to reach the center if cell density is greater than 10% center.

Yang et al.[14] used agarose to fabricate transplants in microbead, rod and slab configurations.

Various kinds of bioartificial pancreas (BAP) have been developed in the past. There have been many disputes about the advantages and disadvantages of each BAP. However, little attention has been paid to the shape of the devices. In this study, three different shaped BAPs were made of the same material, agarose hydrogel. These are microbead-, rod- and disc-shaped BAPs, which are comparable to microcapsules, hollow fibre diffusion chambers and disc-shaped diffusion chambers, respectively, in shape. Numerical analyses showed that insulin release kinetics depended greatly on the thickness of the gel membrane but not on the shape of the agarose hydrogel. These results suggest that the shape of the BAPs determines the in vivo functioning period of the BAPs and that the microbead is the most suitable shape for the BAP.

The authors reported that "small differences such as oxygen tension and nutrients supply drastically affect the fate of encapsulated islets." Theoretical modeling shows that the dimensions of all three implants do not permit oxygen to reach the center if cell density is greater than 10%.

The following table summarizes prior approaches, giving several quantities for comparison:

total volume per implant is given in cubic millimeters ($\mu$l); the volume is determined for the entire transplant including membranes as well as core tissue density is given as a percent of the total volume; assuming an islet diameter of 150 $\mu$m when islet number is given or assuming $2 \times 10^8$ cells per $\mu$l when cell number is given oxygen is determined at the center of the implant furthest from the surface;

using measurements (when available) or the equations of Colton et al.[5] assuming 10% cell density retrievability, whether the implant(s) can easily be removed

| | shape | critical dimention (mm) | other dimention (mm) | volume (mm3) | islets per transplant count | tissue density (%) | O2 at center Y/N | Retrievable Y/N |
|---|---|---|---|---|---|---|---|---|
| *spheres coatings and capsules* | | | | | | | | |
| | | diameter (mm) | | volume (mm3) | islets per transplant | tissue density (%) | O2 at center Y/N | Retrievable Y/N |
| Dorian[33] | coating | 0.32 | | 0.02 | 1 | 10.3% | Y | N |
| Sun[72] | capsule | 0.7 | | 0.18 | 1 | 1.0% | N | N |
| *cylinders tubes and fibers* | | | | | | | | |
| | | diameter (min) | length (mm) | volume (mm3) | islets per transplant | tissue density (%) | O2 at center Y/N | Retrievable Y/N |
| Aebischer[59] | tube | 0.5 | 8 | 2 | NA | 0.1% | Y | Y |
| Ash[61] | tube | 50 | 75 | 147188 | NA | NA | N | Y |
| Aung[24] | tube | 2.4 | 40 | 181 | 1000 | 0.8% | N | Y |
| Bodziony[16] | tube | 1 | 20 | 16 | 200 | 1.8% | N | Y |
| Gaskill[64] | tube | NA | NA | NA | NA | NA | N | Y |
| Inoue[25] | tube | 2.5 | 40 | 196 | 2000 | 1.4% | N | Y |
| Jordan[65] | tube | 4 | NA | NA | NA | NA | N | Y |
| Kopchick[66] | tube | 1.2 | 10 | 11 | NA | 0.1% | N | Y |
| Lacy[8] | tube | 0.73 | 20 | 8 | 1000 | 16.9% | N | Y |
| Lanza[67] | tube | 1.22 | 20 | 23 | 316 | 1.9% | N | Y |
| Laue[54] | tube | 0.62 | 30 | 9 | 5 | 0.1% | N | Y |
| Loeb[68] | tube | NA | NA | NA | NA | NA | N | Y |
| Penfornis[69] | tube | 1.22 | 20 | 23 | 316 | 1.9% | N | Y |
| Scharp[11] | tube | 1 | 15 | 12 | 50 | 0.6% | N | Y |
| Schrezenmeir[18] | tube | 0.62 | 30 | 9 | 10 | 0.2% | N | Y |
| Tze[70] | tube | 1.1 | 25 | 24 | 25 | 0.1% | N | Y |
| Yang[14] | tube | 0.9 | 20 | 13 | 100 | 1.1% | N | Y |
| *planar configurations sheets, discs and slabs* | | | | | | | | |
| | | thickness (mm) | diameter (mm) | volume (mm3) | islets per transplant | tissue density (%) | O2 at center Y/N | Retrievable Y/N |
| Andersson[60] | disc | 0.28 | 6 | 8 | 400 | 7.1% | Y | Y |
| Bae[63] | disc | 1 | 40 | 1256 | 20000 | 2.2% | N | Y |
| Ohgawara[55] | disc | NA | NA | NA | NA | 2.0% | N | Y |
| Scharp* | disc | 0.22 | 6 | 6 | 2000 | 45.4% | Y | Y |
| Scharp* | disc | 0.22 | 6 | 6 | 500 | 11.3% | Y | Y |
| Yang[14] | disc | 2 | 15 | 353 | 600 | 0.2% | N | Y |
| THIS INVENTION | sheet | 0.3 | 50 | 589 | 146144 | 35.0% | Y | Y |

*This work is unpublished under David Scharp's name; however, some data and micrographs have appeared in a popular account of islet transplant research (note 9) and as "some very recent preliminary results" cited in Colton's review (5). The disc with 2000 islets corresponds to Figs. 16a and b in Colton, and the disc with 500 islets corresponds to Fig. 16c, in which each islet is individually encapsulated before being put in the disc, accounting for the lower tissue density.

Prior to the present invention, no bioartificial implant was both (1) small enough in linear dimention to allow effective passive oxygen diffusion into medium density tissue and (2) large enough in volume to contain over 2000 islets.

NOTES

1. London, N. J., Robertson, G. S., Chadwick, D. R., Johnson, P. R., James, R. F., and Bell, P. R., *Human pancreatic islet isolation and transplantation*. Clin Transplant, 1994. 8(5): p. 421–59.

Federlin, K. F., Islet transplantation. *The connection of experiment and clinic exemplified by the transplantation of islets of Langerhans*. Exp Clin Endocrinol, 1993. 101(6): p. 334–45.

2. Lysaght, M. J., Frydel, B., Gentile, F., Emerich, D., and Winn, S., *Recent progress in immunoisolated cell therapy*. J Cellular Biochem, 1994. 56: p. 196–203.

3. Clayton, H. A., James, R. F., and London, N. J., *Islet microencapsulation: a review*. Acta Diabetol, 1993. 30(4): p. 181–9.

4. Colton, C. K. and Avgoustiniatos, E. S., *Bioengineering in development of the hybrid artificial pancreas*. J Biomech Eng, 1991. 113(2): p. 152–70.

5. Colton, C. K., *Implantable Biohybrid Artificial Organs*. Cell Transplant, 1995. 4(4): p. 415–436.

6. de Vos, P., Wolters, G., Fritschy, W., and Van Schilfgarde, R., *Obstacles in the application of microencapsulation in islet transplantation*. int J Artif Organs, 1993. 16: p. 205–212.

Reach, G., *Artificial and bioartificial replacement of the endocrine pancreas*. Artif Organs, 1992. 16(1): p. 61–70.

Reach, G., *Bioartificial pancreas*. Transplant Proc, 1994. 26(2): p. 397–8.

Vanholder, R. and Ringoir, S., *Bicartificial pancreas and liver: a review* [*editorial*]. Int J Artif Organs, 1991. 14(7): p. 398–402.

7. Jain, K., Yang, H., Cai, B. R., Haque, B., Hurvitz, A. I., Diehl, C., Miyata, T., Smith, B. H., Stenzel, K., Suthanthiran, M., and ea, a., *Retrievable, replaceable, macroencapsulated pancreatic islet xenografts. Long-term engraftment without immunosuppression.* Transplantation, 1995. 59(3): p. 319–24.

8. Lacy, P. E., Hegre, O. D., Gerasimidi-Vazeou, A., Gentile, F. T., and Dionne, K. E., *Maintenance of Normoglycemia in Diabetic Mice by Subcutaneous Xenografts of Encapsulated Islets.* Science, 1991. 254: p. 1782–1784.

9. Lacy, P. E., *Treating Diabetes with Transplanted Cells.* Scientific American No. 273 (1995)

10. Kessler, D. A., Siegel, J. P., Noguchi, P. D., Zoon, K. C., Feiden, K. L., and Woodcock, J., *Regulation of Somatic-cell Therapy and Gene Therapy by the Food and Drug Administration.* N Eng J Med, 1993. 329: p. 1169–73.

Noguchi, P. D., Cell *Transplantation and Federal Regulation.* Cell Transplant, 1995. 4(4): p. 411–414. "It also seems quite clear that when the source material of organs and tissues in nonhuman, for example of porcine origin, FDA oversight will be involved."

11. Scharp, D. W., Swanson, C. J., Olack, B. J., Latta, P. P., Hegre, O. D., Doherty, E. J., Gentile, F. T., Flavin, K. S., Ansara, M. F., and Lacy, P. E., *Protection of encapsulated human islets implanted without immunosuppression in patients with type I or type II diabetes and in nondiabetic control subjects.* Diabetes, 1994. 43(9): p. 1167–70. Performed under investigator FDA IND (BB-IND 5103).

12. In reference 8, hypoglycemia during GTT was disclosed in the question period following presentation of this paper.

13. Chicheportiche, D. and Reach, G., *In vitro kinetics of insulin release by microencapsulated rat islets: effect of the size of the microcapsules.* Diabetologia, 1988. 31: p. 54–57.

Fritschy, W. M., Wolters, G. H., and van Schilfgaarde, R., *Effect of alginate-polylysine-alginate microencapsulation on in vitro insulin release from rat pancreatic islets.* Diabetes, 1991. 40(1): p. 37–43.

Horcher, A., Zekorn, T., Siebers, U., Bretzel, R., Zimmermann, U., and Federlin, K., *Insulin release from different models of a bioartificial pancreas (Microencapsulation vs. Macroencapsulation vs. Alainate Coating).* Cell Transplantation, 1992. 1(2/3): p. 175.

14. Yang, H., Iwata, H., Shimizu, H., Takagi, T., Tsuji, T., and Ito, F., *Comparative studies of in vitro and in vivo function of three differe.nt shaped bioartificial pancreases made of agarose hydrogel.* Biomaterials, 1994. 15(2): p. 113–20.

15. Sarver, J. G. and Fournier, R. L., *Numerical investigation of a novel spiral wound membrane sandwich design for an implantable bioartificial pancreas.* Comput Biol Med, 1990. 20(2): p. 105–19.

16. Bodziony, J., *Bioartificial endocrine pancreas: foreign-body reaction and effectiveness of diffusional transport of insulin and oxygen after long-term implantation of hollow fibers into rats.* Res Exp Med, 1992. 192(5): p. 305–16.

17. Gero, L., Kirchgessner, J., Kunz, L. A., Mueller-Klieser, W., Laue, C., and Schrezenmeir, J., *PO2-gradients in isolated piscine islets: effect of fluid convection and barium-alginate encapsulation.* Cell Transplantation, 1992. 1(2/3): p. 165.

18. Schrezenmeir, J., Kirchgessner, J., Gero, L., Kunz, L. A., Beyer, J., and Mueller-Klieser, W., *Effect of microencapsulation on oxygen distribution in islets organs.* Transplantation, 1994. 57(9): p. 1308–14.

19. Chen, K., Ng, C. E., Zweier, J. L., Kuppusamy, P., Glickson, J. D., and Swartz, H. M., *Measurement of the intracellular concentration of oxygen in a cell perfusion system.* Magn Reson Med, 1994. 31(6): p. 668–72.

20. Sawhney, A. S., Pathak, C. P., and Hubbell, J. A., *Interfacial photopolymerization of poly(ethylene glycol)-based hydrogels upon alginate-poly(1-lysine) microcaosules for enhanced bcocompatibility.* Biomaterials, 1993. 14(13): p. 1008–16.

21. Aomatsu, Y., Nakajima, Y., Iwata, H., Takagi, T., Amemiya, H., Kanehiro, H., Hisanaga, M., Fukuoka, T., Yoshimura, A., Kido, K., and et, a., *Indefinite graft survival of discordant islet xenografts in the NOD mouse with acarose macroencapsulation and 15-deoxyspregualin.* Transplant Proc, 1994. 26(2): p. 805–6.

Iwata, H., Takagi, T., Kobavashi, K., Yana, H., and Ito, F., *Immunoisolactive effectiveness and limitation of agarose in a bioartificial pancreas.* Transplant Proc, 1994. 26(2): p. 789.

22. Iwata, H., Takagi, T., Kobayashi, K., Oka, T., Tsuji, T., and Ito, F., *Strategy for developing microbeads applicable to islet xenotrarnsplantation into a spontaneous diabetic NOD mouse.* J Biomed Mater Pes, 1994. 28(10): p. 1201–7.

Takagi, T., Iwata, H., Kobayashi, K., Oka, T., Tsuji, T., and Ito, F., *Development of a microcapsule applicable to islet xenotransplantation.* Transplant Proc, 1994. 26(2): p. 801.

23. Crooks, C. A., Douglas, J. A., Broughton, R. L., and Sefton, M. V., *Microencapsulation of mammalian cells in a HEMA-MMA copolymer: effects on capsule morphology and permeability.* J Biomed Mater Res, 1990. 24(9): p. 1241–62.

Lamberti, F., Evangelista, R., Blysniuk, J., Wheatley, M., and Sefton, M., *Microencapsulation of Mammalian Cells in Polyacrylates.* Appl Biochem Biotechnol, 1984. 10(99): p. 101–104.

Sefton, M. V., *Encapsulation of live animal cells; in semipermeable polymeric membrane.* U.S. Pat. No. 4,353,888 (1982)

Stevenson, W. T. and Sefton, M. V., *Graft copolymer emulsions of sodium alginate with hydroxyalkyl methacrylates for microencapsulation.* Biomaterials, 1987. 8(6): p. 449–57.

24. Aung, T., Inoue, K., Kogire, M., Doi, R., Kaji, H., Tun, T., Hayashi, H., Echigo, Y., Wada, M., Imamura, M., and et, al., *Comparison of various gels for immobilization of islets in bioartificial pancreas using a mesh-reinforced polyvinyl alcohol hydrogel tube.* Transplant Proc, 1995. 27(1): p. 619–21.

25. Inoue, K., Fujisato, T., Gu, Y. J., Burozak, K., Sumi, S., Kogire, M., Tobe, T., Uchida, K., Nakai, I., Maetani, S., and et, a., *Experimental hybrid islet transplantation: application of polyvinyl alcohol membrane for entrapment of islets.* Pancreas, 1992. 7(5): p. 562–8.

26. Tatarkiewicz, K., Sitarek, E., Fiedor, P., Sabat, M., Morzycka-Michalik, M., and Orlowski, T., *Successful rat-to-mouse xenctransplancation of Langerhans islets microencapsulated within a protamine-heparin membrane.* Transplant Proc, 1994. 26(2): p. 807–8.

27. Desai, N., Soon-Shiong, P., Sandford, P., and Heintz, R., *Ionically Covalently Crosslinked and Crosslinkable Biocompatible Encapsulation Compositions and Methods.* U.S. Pat. No. 5,334,640 (1994).

28. Lim, F. and Sun, A. N., *Microencapsulated islets as a bioartificial endocrine pancreas.* Science, 1980. 210: p. 908.

29. Cochrum, K., C., Dorian, R., E., and Jemtrud Susan, A., *Multiple Layer Alginate Coatings of Biological Tissue for Transplantation.* U.S. patent application Ser. No. 08/186, 327 (1994).

30. Martinsen, A., Storre, I., and Skjak-Braek, G., *Alginate as immobilization material: III. Diffusional properties*. Biotechnology and Bioengineering, 1992. 39: p. 186–194.

31. Skjak-Braek, G., *Alginates: biosyntheses and some structure-function relationships relevant to biomedical and biotechnological applications*. Biochem Soc Trans, 1992. 20(1): p. 27–33.

32. Martinsen, A., Skjak-Braek, G., and Smidsrod, O., *Alginate as immobilization material: I. Correlation between chemical and physical properties of alginate gel beads*. Biotechnology and Bioengineering, 1989. 33: p. 79–89.

Skjak-Braek, G., Murano, E., and Paoletti, S., *Alginate as immobilization material: II. Determination of Polyphenol Contaminants by fluorescence spectroscopy, and evaluation of methods for their removal*. Biotechnology and Bioengineering, 1989. 33: p. 90–94.

33. Dorian, P., E., Cochrum, K., C., and Jemtrud Susan, A., *Non-fibrogenic high mannuronate alginate coated transplants, processes for their manufacture, and methods for their use*. U.S. Pat. No. 5,429,821 (1995)

34. Cochrum, K., Jemtrud, S., and Dorian, P., *Successful Xencgrafts in Mice with Microencapsulated Rat and Dog Islets*. Transplant Proc, 1995. IN PRESS.

35. Ziminermann, U., Klock, G., Federlin, K., Hannig, K., Kowalski, M., Bretzel, R. G., Horcher, A., Entenmann, H., Sieber, U., and Zekorn, T., *Production of mitogen-contamination free alginates with variable ratios of mannuronic acid to guluronic acid by free flow electrophoresis*. Electrophoresis, 1992. 13(5): p. 269–74.

36. Zekorn, T., Klock, G., Horcher, A., Siebers, U., Wohrle, M., Kowalskli, M., Arnold, M. W., Federlin, K., Bretzel, R. G., and Zimmermann, U., *Lymphoid activation by different crude alginates and the effect of purification*. Transplant Proc, 1992. 24(6): p. 2952–3.

37. Darquy, S., Pueyo, M. E., Capron, F., and Reach, G., *Complement activation by alginate-polylysine microcapsules used for islet transplantation*. Artif organs, 1994. 18(12): p. 898–903.

Lanza, R. P., Kuhtreiber, W. M., Ecker, D., Staruk, J. E., and Chick, W. L., *Xenotransplantation of porcine and bovine islets without immunosuppression using uncoated alginate microspheres*. Transplantation, 1995. 59(10): p. 1377–84.

38. Skjak-Braek, G., *Alginates: biosyntheses and some structure-function relationships relevant to biomedical and biotechnological applications*. Biochem Soc Trans, 1992. 20(1): p. 27–33.

Otterlei, M., Ostgaard, K., Skjak-Braek, G., Smidsrod, O., Soon-Shiong, P., and Espevik, T., *Induction of cytokine production from human monocytes stimulated with alginate*. J Immunother, 1991. 10(4): p. 286–91.

Soon-Shiong, P., Otterlei, M., Skjak-Braek, G., Smidsrod, O., Heintz, R., Lanza, R. P., and Espevik, T., *An immunologic basis for the fibrotic reaction to implanted microcapsules*. Transplant Proc, 1991. 23(1 Pt 1): p. 758–9.

Soon-Shlona, P., Feldman, E., Nelson, R., Kontebedde, J., Smidsrod, O, Skjak-Braek, G., Espevik, T., Heintz, R., and Lee, M., *Successful reversal of spontaneous diabetes in dogs by intraperitoneal microencapsulated islets*. Transplantation, 1992. 54(5): p. 769–74.

39. Wahoff, D. C., Stephanian, E., Gores, P. F., Soon-Shiong, P., Hoper, C., Lloveras, J. K., and Sutherland, D. E., *Intraperitoneal transplantation of microencapsulated canine islet allografts with short-term, low-dose cyclosporine for treatment of pancreatectomy-induced diabetes in dogs*. Transplant Proc, 1994. 26(2): p. 804.

40. Lamberton, R., P. and Lipsky, M., H., *Neovascularization; sponge surrounding ligated blood vessel and semipermeable cell container*. U.S. Pat. No. 4,699,141 (1987)

41. Marchetti, P., Scharp, D. W., McLear, M., Finke, E. H., Olack, B., Swanson, C., Giannarelli, R., Navalesi, R., and Lacy, P. E., *Insulin inhibits its own secretion from isolated, perifused human pancreatic islets*. Acta Diabetologica, 1995. 32: p. 75–77.

42. Dalmasso, A. P., *The complement system in xenotransplantation*. Irnmunopharmacology, 1992. 24(2): p. 149–60.

43. Satake, M., Korsgren, O., Ridderstad, A., Karlsson-Parra, A., Wallren, A. C., and Moller, E., *Immunological characteristics of islet cell xenotransplantation in humans and rodents*. Immunol Rev, 1994. 141(211): p. 191–211.

44. Hamelmann, W., Gray, D. W., Cairns, T. D., Ozasa, T., Ferguson, D. J., Cahill, A., Welsh, K. I., and Morris, P. J., *Immediate destruction of xenogeneic islets in a primate model*. Transplantation, 1994. 58(10): p. 1109–14.

45. Zekorn, T., Entenmann, H., Horcher, A., Siebers, U., Klock, G., Zimmermann, U., Federlin, K., and Bretzel, R. G., *Lymphoid activation by micro- and macroencapsulated islets during mixed lymphocyte islet culture*. Acta Diabetol, 1993. 30(4): p. 238–42.

46. Grohn, P., Klock, G., Schmitt, J., Zimmermann, U., Horcher, A., Bretzel, R. G., Hering, B. J., Brandhorst, D., Brandhorst, H., Zekorn, T., et al., *Large-scale production of Ba(2+)-alginate-coated islets of Langerhans for immunoisolation*. Exp Clin Endccrinol, 1994. 102(5): p. 380–7.

47. Horcher, A., Zekorn, T., Siebers, U., Klock, G., Schnettler, R., Arnold, M., Federlin, K., Zimmermann, U., and Bretzel, R. G., *Insulin release from different models of a bioartificial pancreas (microencapsulation versus alginate-coating)*. Transplant Proc, 1992. 24(6): p. 2950–1.

48. de Vos, P., Wolters, G. H., and van Schilfgaarde, R., *Possible relationship between fibrotic overgrowth of alginate-polylysine-alginate microencapsulated pancreatic islets and the microcapsule integrity*. Transplant Proc, 1994. 26(2): p. 782–3.

49. Siebers, U., Zekorn, T., Bretzel, R. G., Planck, H., Renardy, M., Zschocke, P., and Federlin, K., *Histocompatibility of semipermeable membranes for implantable diffusion devices (boartiflcial pancreas)*. Transplant Proc, 1990. 22(2): p. 834–5.

Wong, H. and Chang, T. M., *The microencapsulation of cells within alginate poly-L-lysine microcapsules prepared with the standard single step drop technique: histologically identified membrane imperfections and the associated graft rejection*. Biomater Artif Cells Immobilization Biotechnol, 1991. 19(4): p. 675–86.

50. Yderstraede, K. and Starklint, H., *Transplantation of encapsulated neonatal rat islets to nude mice and NMRI mice using the renal subcapsular space. Abstract from 14th Workshop of the study group Artificial Insulin Delivery Systems, Pancreas and Islet Transplantation (AIDSPIT) of the European Association for the Study of Diabetes (EASD)*. Igls, Austria, Jan. 30–31, 1995. Horm Metab Res, 1995. 27(1): p. 47–66.

51. Juang, J. H., Bonner-Weir, S., Wu, Y. J., and Weir, G. C., *Beneficial influence of glycemic control upon the growth and function of transplanted islets*. Diabetes, 1994. 43(11): p. 1334–9.

52. Hering, B. J., Browatzki, C. C., Schultz, A. O., Bretzel, R. C., and Federlin, K., *Islet Transplant Registry report on adult and fetal islet allografts*. Transplant Proc, 1994. 26(2): p. 565–8.

53. Rosenberg, L., *In Vivo Cell Transformation: Neogenesis of Beta Cells from Pancreatic Ductal Cells*. Cell Transplant, 1995. 4(4): p. 371–383. See page 375.

54. Miettinen, P. J., Otonkoski, T., and Voutilainen, R., *Insulin-like growth factor-II and transforming growth* factor-alpha in developing human fetal pancreatic islets. J Endocrinol, 1993. 138(1): p. 127–36.

Otonkoski, T., Beattie, G. M., Lopez, A. D., and Havek, A., *Use of hepatocyte growth factor/scatter factor to increase transplantable human fetal islet cell mass.* Transplant Proc, 1994. 26(6): p. 3334.

55. Laue, C., Zimmermann, U., Biesalski, H. K., Beyer, J., and Schrezenmeir, J., *Antioxidatve vitamins reduce fibrous tissue overgrowth of the bioartificial pancreas.* Transplant Proc, 1995 27(2): p. 1875–6.

56. Ohgrwara, H., Miyazaki, J.-i., Karibe, S., Tashiro, F., Akaike, T., and Hashimoto, Y., *Embedded-culture of Pancreatic beta-cells derived from transgenic mouse insulinoma as a potential source for xenotransplantation using a diffusion chamber.* Cell Transplant, 1995. 4(3): p. 307–313.

57. Aebischer, P. and Winn, S. R., *In vivo delivery of active factors by co-cultured cell implants; semipermeable membranes.* U.S. Pat. No. 5,182,111 (1993)

58. Bellamkonda, R. and Aebischer, P., *Review: Tissue engineering in the Nervous System.* Biotech Bioeng, 1994. 43(543–554).

Colton (note 5) See the introduction section, especially the second paragraph, and references cited therein.

Lysaght (note 2) Table 1.

Nyberg, S. L., Shatford, R. A., Hu, W. S., Payne, W. D., and Cerra, F. B., *Hepatocyte culture systems for artificial liver support: implications for critical care medicine (bioartificial liver support).* Crit Care Med, 1992. 20(8): p. 1157–68.

59. Scharp, D. W., Mason, N. S., and Sparks, R. E., *Islet Immuno-isolation: the use of hybrid artificial organs to prevent islet tissue rejection.* World J Surg, 1984. 8: p. 221–229.

60. Aebischer, P. and Wahlberg, L., *Method of encapsulating cells in a tubular extrudate; coextrusion of semipermeable polymeric membrane and cells.* U.S. Pat. No. 5,284,761 (1994). For the comparison table, we estimated the tube diameter and length from the figures and discussion (column 5, lines 15–17). Tissue density is based on $1 \times 10^5$ cells/ml reported in the patent (column 8, line 10) compared with packed tissue density of 2 to $5 \times 10^8$ cells/ml.

61. Andersson, A., Ei-irik, D. L., Hellerstrom, C., Johnson, R. C., and Pipeleers, D. G., *Morphology of encapsulated human pancreacic islets transplanted into nude mice.* Transplant Proc, 1994. 26(2): p. 802–3. The core of this device is high density packed islets reenforced with polyester fibers. The overall density and thickness of the device are determined assuming that the core is 0.12 mm thick and the two laminated double membranes are 0.08 mm thick.

62. Ash, S. R. and Loeb, M. P., *Body cavity access device containing a hormone source.* U.S. Pat. No. 4,402,694 (1983). For the comparison table, we estimated the tube diameter and length from the figures and discussion (column 5, lines 3 and 12; claim 12). Tissue density is not reported.

63. Aung, T., Inoue, K., Kogire, M., Sumi, S., Fujisato, T., Gu, Y. J., Shinchara, S., Hayashi, H., Doi, R., Imamura, M., et al., *Improved insulin release from a bioartificial pancreas using mesh-reinforced polyvinyl alcohol hydroagel tube: immobilization of islets in agarose gel.*

64. Bae, Y. H. and Kim, S. W., *Implantable and refillable biohybrid artificial pancreas; for use in the treatment of diabetes.* U.S. Pat. No. 5,262,055 (1993). The thickness is calculated from numbers in Example 5 and the assumption that 80% of the surface is channels, and the membranes are each 0.05 mm thick.

65. Gaskill, H. V., III, *Intravascular artificial organ.* U.S. Pat. No. 4,911,717 (1990).

66. Jordan, G. P. W., *Artificial gland.* U.S. Pat. No. 3,093,831 (1963).

67. Kopchick, J. J., Leung, F. C., Livelli, T. J., and Malavarca, R. H., *Encapsulated mouse cells transformed with avian retrovirus-bovine growth hormone DNA, and a method of administering bgh in viva; administer by hollow fiber filled with recombinant mouse cell suspension; lactation.* U.S. Pat. No. 4,686,098 (1987).

68. Lanza, R. P., Borland, K. M., Lodge, P., Carretta, M., Sullivan, S. J., Muller, T. E., Solomon, B. A., Maki, T., Monaco, A. P., and Chick, W. L., *Treatment of severely diabetic pancreatectcmized dogs using a diffusion-based hybrid pancreas.* Diabetes, 1992. 41(7): p. 886–9.

Lanza, P. P., Sullivan, S. J., and Chick, W. L., *Perspectives in Diabetes: Islet transplantation with immunoisolation.* Diabetes, 1992. 41: p. 1503–10.

69. Loeb, M. P., *Artificial endocrine gland containing hormone-producing cells.* U.S. Pat. No. 4,378,016 (1983).

70. Penfornis, F., Icard, P., Gotheil, C., Boillot, J., Cornec, C., Barrat, F., Altman, J. J., and Cochin, J. V., *Bioartificial pancreas in pigs.* Horm Metab Res Suppl, 1990. 25(2): p. 200–2.

71. Tze, W. J., Cheung, S. S., Tai, J., Bissada, N., Tsang, A., and Yep, W., *Prolongation of pig islet xenograft survival in polysulfone fiber coil.* Transplant Proc, 1994. 26(6): p. 3510–1.

72. Lim, F., *Microencapsulation of Living Cells and Tissues.* Appl Biochem Biotechnol, 1984. 10(99): p. 81–85.

Chen, C. F., Chern, H. T., Leu, F. J., Chang, T. M., Shian, L. R., and Sun, A. M., *Xenotransplantation of microencapsulated canine islets into diabetic rats.* Artif Organs, 1994. 18(3): p. 193–7.

SUMMARY OF THE INVENTION

The present invention concerns a bioartificial implant and methods for its manufacture and use. The dimensions of the bioartificial implant are such that cell viability may be maintained by passive diffusion of nutrients, and preferably, such that a high cell density can be maintained. The dimensions of the bioartificial implant are also such that the bioartificial implant is macroscopic and is easily retrievable from the host and is large enough to contain a significant fraction of the tissue required to achieve the desired therapeutic effect. The permeability of the bioartificial implant is such that cell viability may be maintained by passive diffusion of nutrients, and preferably such that passive diffusion of secreted cell products permits rapid response to changing physiological conditions. At the same time, the permeability of the membrane sufficiently impedes diffusion of antibody and complement to prevent lysis of the implanted cells, even when the tissue is a xenograft. The bioartificial implant is biocompatible, meaning it produces no foreign body reaction.

The dimensions of the present bioartificial implant, when in a thin sheet configuration, are such that the surface area of a side of a sheet is at least 30 mm$^2$, preferably at least 2.5 cm$^2$ and more preferably 10 cm$^2$, as defined by either (a) the diameter (if the sheet is circular) or (b) the area determined by the method of converging polygons. Although the maximum dimensions can be that which is tolerated by the patient into whom the implant is placed, for ease of fabrication and economy of implanted cells, the maximum surface area of a side of the present thin sheet implant may be 400 cm$^2$, more preferably 300 cm$^2$ and most preferably 250 cm$^2$ (for a human patient).

In the present bioartificial implant, the cell density is that which can be contained within a thin alginate gel coat. Preferably, the cell density is at least 10%, more preferably 20% and most preferably at least 35% by volume.

The surface of the bioartificial implant is biocompatible. We have found that attempts to induce neovascularization at the surface of the implant with synthetic polymers[60,3] are less than ideal for long term implant viability. We have found that implants that are neutral (causing neither fibrosis nor neovascularization) have been shown to last over a year with minimal decay of function[12].

The bioartificial implant is described using the terms "core," "coat" and "overcoat." The core comprises the living tissue, trophic factors and nurse cells, alginate polymer crosslinked with a multivalent cation such as calcium, and a fiber mesh for strength. The coat comprises alginate polymer crosslinked with a multivalent cation that serves to control permeability. The overcoat comprises alginate polymer crosslinked with a multivalent cation that serves to render the bioartificial implant biocompatible.

One aspect of the present invention is its shape or configuration. Previous inventions have responded to inherent limitations on diffusion of oxygen by lowering cell densities within the bioartificial implant. We have found that an effective implant must have medium to high tissue densities to minimize the volume of the total bioartificial implant, and that the thickness of a sheet or slab must be very small to permit effective oxygen diffusion. The sum of the core, coat and overcoat thicknesses should be less than 400 $\mu$m, preferably 350 $\mu$m or less, and more preferably no more than 300 $\mu$m. The coat and overcoat thickness should be minimized so that the tissue quantity may be maximized. We have found that the coat and overcoat thicknesses may be from 10 to 100 $\mu$m thick, preferably from 10–80 $\mu$m, and most preferably from 10–50 $\mu$m. Biocompatible implant coat thicknesses of only tens of $\mu$m have never been before reported. The length and width of the bioartificial implant on the other hand should be maximized to permit the greatest possible volume of living tissue to be included in the bioartificial implant and to permit easy retrieval.

Another aspect of the present invention is the material out of which the bioartificial implant is constructed. Biocompatible purified alginates have been described, but have only been used to produce coated and encapsulated implants. No bioartificial implant has been described using aiginate in a thin sheet. The properties of alginate gel can be controlled by selecting the G and M content, the chain length, the alginate concentration, and counterions (e.g. calcium, zinc, barium or a combination thereof). Alginate in the core is compatible with living tissue. The fabrication of alginate hydrogels is compatible with cell viability. Sodium alginate used to fabricate the core can be mixed with trophic factors and nurse cells along with the secreting tissue before gelation with multivalent cations to provide a supportive environment. Alginate for the coating can be selected as to chain length and G and M fractions and be gelled with various multivalent cations to control the permeability of the coat. Alginate for the overcoat can be selected so as to maximize the biocomoatibility of the bioartificial implant.

The bioartificial implant is fabricated using a series of molds constructed with frit materials that can be molded or milled, and membranes. This allows diffusion of chelating agents (e.g., sodium citrate) or multivalent cation gelling agents (e.g., calcium, barium or zinc chlorides) to liquify and gel, respectively, the core, coat and overcoat. The manufacturing process makes use only of ions known to be compatible with the implanted cells.

Although many variations of the method exist, the essence of the process is simple. The shape of the core, coat and overcoat are molded while the alginate is liquid. The core and coat (and later the coat and overcoat) are crosslinked by simply contacting liquid alginate containing a small amount of chelating agent to the gelled layer. The chelating agent diffuses into the gelled layer and partially liquifies it. When a cationic crosslinking agent is subsequently added, a tight bond is formed between the layers. The outer surface is made very smooth through the simple step of wetting the mold with crosslinking agent solution before contacting the mold with the liquid coat or overcoat. We have found that contact with the membrane thus wetted immediately produces a very smooth surface.

Because the coat and overcoat are fabricated from liquids, they can be made very thin, even as thin as a few $\mu$m.

We have invented a bioartificial implant of dimensions never before achieved, with many attendant advantages. For example, one object of the present invention is to provide a bioartificial implant that is easily retrievable from the host.

Another object of the present invention is to provide a bioartificial implant in a thin sheet configuration permitting both high tissue densities and diffusion to the tissue cells of the amounts of nutrients, oxygen and other substances required for cellular health, longevity and effective function after implantation.

Another object of the present invention is to provide a bioartificial implant in an easily retrievable thin sheet configuration, permitting both high tissue densities and effective diffusion of nutrients into and cellular products out from the implant.

Another object of the present invention is to provide a bioartificial implant in the configuration of a thin sheet of viable, physiologically active, tissue cells for implantation which is physiologically acceptable to the host and which effectively provides prolonged protection of the tissue cells, after implantation, from destruction by the host immune system.

Another object of the present invention is to provide an effective implant coating material in a retrievable thin sheet configuration which is physiologically acceptable, non-fibrogenic and non-toxic to host tissue.

Another object of the present invention is to provide a bioartificial implant containing trophics such as nurse cells, ground substances, nutrients, hormones or oxygen carriers to support the cellular health, longevity and effective function of the implant after implantation.

A further object of the present invention is to provide a novel manufacturing process for effectively enclosing an implant (e.g., cells, tissues and/or other biological substances) with a barrier or membrane which is physiologically acceptable, non-fibrogenic and non-toxic to host tissue, which may provide a complete barrier coating with a controlled thickness and controlled permeability to intermediately sized proteins, and which is easily retrievable.

In summary, the present invention may comprise an implant core having a thin sheet configuration comprising viable, physiologically active, tissue cells and a crosslinked alginate gel and optionally, trophic factors and nurse cells, and optionally, a fiber mesh support. The alginates are preferably free from fibrogenic concentrations of impurities.

The bioartificial implant may have a coat and overcoat to control permeability and enhance biocompatibility. The implant sheet is thin and may be permeable enough to provide a physiologically acceptable oxygen tension at the center of the sheet when implanted in a suitable site in a human or animal subject. The thinness and permeability of the implant allows diffusion of nutrients, oxygen, metabolic waste products and secreted tissue products. The implant preferably inhibits diffusion of antibody and complement.

Preferably, the coat permits rapid diffusion of substances below 50 Kd and significantly inhibits diffusion of substances over 100 kD. The coat is also very thin, preferably approximately 10–50 μm. The coat may comprise and thus, be constructed with, for instance, short chain, high M alginate gelled with a mixture of calcium and zinc ions.

Suitable cells for the present implant include, for example, pancreatic islets, renal cortex cells, parathyroid cells, thyroid cells, adrenal cells, hepatic cells, cells of various origins that have been genetically engineered to secrete useful substances, cells of various origins that have been genetically engineered to metabolize harmful substances, tissues, and the like.

The process of the present invention for making a biocompatible implant may comprise the steps of:

(a) forming a core containing viable, physiologically active, tissue donor cells in an alginate gel, preferably in a thin, sheet-shaped mold and more preferably by crosslinking an alginate solution containing the cells;

(b) contacting the core with a second alginate solution containing a concentration of citrate sufficient to induce at least partial liquification of the alginate gel in the core;

(c) crosslinking the second alginate solution and liquefied alginate gel in the core to form a coat layer bonded to the core, and thus, the biocompatible implant, preferably by diffusing a crosslinking agent into the second alginate solution and liquefied alginate gel in the core.

Optionally, crosslinking step (c) may comprise contacting the inner surface of the mold with an aqueous calcium ion solution to create a smooth outer surface on the biocompatible implant. This optional step may be performed in addition to the diffusing step. A further option is to repeat step (b) with a third alginate solution containing sufficient citrate to induce at least partial liquification of the alginate gel in the coat, and repeat step (c) by crosslinking the third alginate solution and liquefied alginate gel in the coat to form an overcoat layer bonded to the coat. The coat of the biocompatible implant may be formed to control permeability, and the overcoat formed to enhance biocompatibility.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a schematic diagram of the thin sheet bioartificial implant.

FIG. 2 is an enlarged schematic diagram cross section of the thin sheer bioartificial implant shown in FIG. 1.

FIG. 3 is an enlarged schematic diagram cross section of the core edge and the coating of the thin sheet bioartificial implant in the coating mold.

FIG. 4 is an enlarged schematic diagram cross section of the core of the thin sheet bioartificial implant in the core mold.

FIG. 5 is an enlarged schematic diagram cross section of the coated thin sheet bioartificial implant in the coating mold.

FIG. 6 is an enlarged schematic diagram cross section of the overcoated thin sheet bioartificial implant in the overcoating mold.

FIG. 7 is a schematic diagram cross section of the mold used for fabrication of the core, coating, and overcoating, shown in separated sections (A), touching (B), and clamped (C).

FIG. 8 is a schematic diagram cross section of the mold used for fabrication of the coating half, shown in separated sections (A) and touching (B).

FIG. 9 is a micrograph of the bioartificial implant core produced using the present invention using polymer spheres to represent islets (~100×).

FIG. 10 is a micrograph of a section of the bioartificial implant core produced using the present invention using polymer spheres to represent islets (~100×).

FIG. 11 is a micrograph of a section of the complete (coated, overcoated) bioartificial implant produced using the present invention using polymer spheres to represent islets

DETAILED DESCRIPTION OF THE INVENTION

The bioartificial implant of the present invention is effective for implantation into a host animal by standard surgical procedures or by use of abdominal trochar and laparoscope.

The term "implant," as used herein, is defined to include all living tissues, cells, and biologically active substances intended to be implanted into the body of a host animal, as well as the act of implanting or transferring these tissues and cells into a host. These tissues and cells include, without limitation, tissue and cells removed from a donor animal, tissue and cells obtained by incubation or cultivation of donor tissues and cells, cells obtained from viable cell lines, cells obtained by genetic engineering, biologically active products of cells and tissues, pharmaceuticals, drugs, enzymes, eutrophics, and the like. Tissues may perform a useful biological function either by secreting a therapeutic or trophic substance or by removing a toxic or harmful one. An example of the latter would be removal of various fatty substances from serum to reduce blood lipid levels.

Any type of tissue or cells for which implantation is desired can be fabricated into a sheet and implanted according to the present invention. The most common tissues for implants are secretory organ tissues, where implantation from a donor organ to a recipient or host animal is desired to at least partially replicate the donor organ's action in the host system. Preferred donor tissues are pancreatic islets, hepatic cells, neural cells, renal cortex cells, vascular endothelial cells, thyroid cells, parathyroid cells, adrenal cells, thymic cells and ovarian cells.

The process of the present invention is described hereinafter for the preparation and implantation of pancreatic islets and islet cells by way of example for purposes of clarity of explanation and not by way of limitation. This process can be equally well applied to other organ tissues as will be readily apparent to a person skilled in the art, with conventional and obvious modification as desired or required to accommodate any uniquely different requirements of the different tissues. Applications of the process to all tissues and cells suitable for implantation are intended to be within the scope of the present invention.

Isolated pancreatic islets (or other cells or tissues suitable for implantation) are prepared by conventional procedures to substantially separate them from extraneous tissue and other donor substances.

In a first step of the process of the present invention, isolated pancreatic islets (or other cells or tissue) are washed with isotonic saline and suspended in solution of purified sodium alginate. The alginate has been purified to make it fully biocompatible as described in prior publications[34,33,35].

The alginate may be prepared with various molecular weights (chain lengths) high in guluronate residues or high in mannuronate residues[30,31,35]. These methods are based on differential binding of homopolymeric M and G blocks to various cations. Selection of (i) the fraction of homomeric C blocks, homomeric M blocks and alternating GM blocks, (ii) the average chain length, (iii) the alginate concentration and (iv) the mixture of cations used to gel the alginate can be used to produce alginate gels with a very large variety of properties. In the following, "alginate" means a solution of alginate selected for desired properties and which may be gellable, "alginate gel" means a crosslinked alginate, and "multivalent cation" means a mixture of multivalent cations such as calcium, barium and zinc selected to give desired properties when used in combination with the selected alginate.

The core alginate is selected for low viscosity in the liquid state (so as not to damage islets during core fabrication), high strength in the gel state (for a strong implant), compatibility with tissue, and compatibility with trophic factors. The core alginate typically consists of alginate (e.g., of from 80 to 800 kD, preferably from 100 to 500 kD, and more preferably from 200 to 400 kD) in a low concentration (preferably from 0.5 to 10%, more preferably from 1.0 to 5% and most preferably about 2.0%), having mixed M and G blocks crosslinked with calcium.

The coat alginate is selected for high viscosity in the liquid state (particularly for the "gum" method), high strength in the gel state (for a strong implant), high permeability for low molecular weight species (e.g., permitting diffusion of molecules and/or complexes having a molecular weight below 150 kD, preferably below 100 kD, and more preferably below 75 kD) and low permeability for high molecular weight species (e.g., inhibiting or prohibiting diffusion of molecules and/or complexes having a molecular weight above 200 kD, preferably above 150 kD, and more preferably above 100 kD). Typically, the coat alginate consists of short chain alginate (e.g., of from 80 to 800 kD, preferably from 100 to 600 kD, and more preferably from 100 to 400 kD) at a high concentration (e.g., 5–40%, preferably 10–30%, more preferably 15–25%), crosslinked with calcium. Preferably, the ratio of M units to G units in the coat alginate is from 0.2:1 to 6:1, more preferably from 0.3:1 to 3:1, and most preferably from 0.4:1 to 1.5:1.

It should be appreciated that molecular weight, concentration and M:G ratio independently affect the viscosity and permeability of the alginate. The desired viscosity and permeability are controlled by simultaneously optimizing all three. In general, the same permeability is found in alginates of a lower concentration when they have a higher M:G ratio. For example, a 25% solution with M:G of 1:1 might have similar properties as a 12% solution with M:G of 2:1.

The overcoat alginate is selected for high permeability and high biocompatibility, typically consisting of alginate of low concentration crosslinked with calcium. Preferably, the overcoat alginate permits diffusion of molecules and/or complexes having a molecular weight below 800 kD, preferably below 400 kD, and more preferably below 200 kD. Typically, the overcoat alginate consists of alginate (e.g., of from 10 to 800 kD, preferably from 20 to 400 kD, and more preferably from 20 to 400 kD) at a low concentration (e.g., 0.5–10%, preferably 1–5%, more preferably 1.5–3%), having a high proportion of M units crosslinked with calcium.

Preferably, the ratio of M units to G units in the coat alginate is from 0.2:1 to 6:1, more preferably from 0.5:1 to 2:1, and most preferably from 0.6:1 to 1.5:1.

The core alginate is selected to provide a suitable environment for the pancreatic islets (or other cells or tissue) and for the trophic factors and nurse cells needed. For example, given the importance of oxygen diffusion, most implants will include hemoglobin or another oxygen carrier in the alginate. Many cells are healthier in the presence of collagen. Other trophic factors may be suitable for particular cells and tissues. The optimal combination of ingredients for the implant core can be evaluated using established cell culture methods.

Once the components of the implant core are selected, they can be combined. Sodium (or potassium) alginate can be used with a low concentration of citrate to keep the mixture completely liquid. Citrate strongly chelates calcium and other multivalent cations so that they cannot crosslink and gel alginate.

FIG. 1 is a schematic diagram of a thin sheet bioartificial implant according to the present invention. An optional core mesh 2 is surrounded by alginate 3.

FIG. 2 is an enlarged schematic diagram cross-section of the thin sheet bioartificial implant of FIG. 1. As illustrated, the optional core mesh 2 is surrounded by alginate 3 and islets 1. Coat alginate layers 4 are in contact with and exterior to the upper and lower surfaces, respectively, of the core alginate 3. Optional overcoat layers 5 are in contact with and exterior to the outer surfaces of the upper and lower surfaces, respectively, of coat alginate layers 4. Layers of mesh 6 are in contact with and exterior to the upper and lower surfaces, respectively, of overcoat layers 5

FIG. 7 is a diagram of a typical mold used for the fabrication of the bioartificial implant. The molds are approximately circular, but also may be oval or any other compact shape. The two halves of the mold, shown separated in FIG. 7A, can be combined by touching their outer annuluses (FIG. 7B) and secured in that position with clamps (FIG. 7C). The bulk of the mold 11 is a frit made from sintered stainless steel (Mott Metalurgical, NO or GT) with a porosity between 0.01 and 5 μm, preferably approximately 0.4 μm. The frit 11 may also be made from sintered glass or ceramic. The frit 11 is thick enough to provide mechanical strength to the entire assembly FIG. 7C. The outer annulus 21, 22 can be made of the same material as the frit 11 (when it is nonfragile, e.g. sintered stainless steel) or of a nonporous rigid material such as stainless steel or ceramic if the frit 11 is fragile. The annulus 21 of the upper mold is flush with the frit 11. The annulus 22 of the upper mold extends out from the frit 11 by a precise amount ranging from 10 μm to 500 μm.

The molds may be used one to three times in the fabrication of the implant, and may come in several dimensions suitable for each stage of the fabrication. A set of molds for a particular fabrication sequence are of similar diameter, except that the inner diameter of annulus 21 will be slightly larger for a mold used in a later step. The increase in inner diameter may vary from 20 μm to several hundred μm (e.g., 300–400 μm), and will typically be about 50 μm. A set of molds for a particular fabrication sequence will have a successively increasing depth of the frit from the annulus of the lower mold 22 to accommodate the formation of successive layers of the implant.

Molds optionally have a membrane 12 attached to their surfaces. The membrane (e.g., Track-etch/Poretics, Livermore, Calif.) can have a pore size of 0.01 μm up to 0.2

μm. FIGS. 8A and 8B are schematic diagram cross-sections of the mold used for fabricating the coating halves. FIG. 8A illustrates the mold in separated sections and FIG. 8B illustrates the mold with the sections touching.

The molds may be either of two types shown in FIGS. 7A, B and C and 8A and B. The mold shown in FIGS. 8A and B may be used to fabricate coat halves. Two premolded coat halves are required to fabricate the implant if premolded coating halves are used. The upper mold half shown in FIG. 8 has an embossed disc so that the mold void defines a sheet with an annular, thicker ring (called a "coat half").

Other fabrication steps may require molds like the ones shown in FIG. 7. The surfaces of both mold halves are preferably flat, and may have mold voids that define perfect sheets.

Changes in the physical properties of alginate in the presence of various ions are exploited in the fabrication methods. Alainate is a polymer of sugar acids. In the presence of monovalent counter ions such as sodium and potassium, alginate solutions are liquid. In the presence of multivalent cations such as calcium, barium and zinc, the alginate solution forms a gel. The gelling mechanism is that the multivalent cations become ionically bonded to two acid groups in the alginate polymer, crosslinking them. Conversely, if a chelating agent such as citrate or EDTA is contacted with an alginate gel, the cross-linking ions become detached from the alginate gel and are sequestered by the chelating agent.

These relations are summarized in the following diagram:

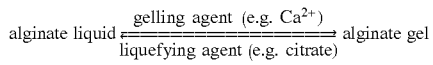

This property of alginate is exploited in three ways.

First, liquid alginate placed in a mold is gelled by allowing calcium (or other suitable multivalent cation(s)) to diffuse through the frit by immersing the apparatus in a solution of calcium chloride (or salt(s) of other suitable multivalent cation(s)).

Second, a liquid alginate is effectively linked to a gelled alginate by a two-step process. The first step involves contacting the gelled alginate with a chelating agent (e.g., citrate, 1–100 mM, preferably 5–50 mM, more preferably approximately 10 mM) present in the liquid alginate. When the liquid alginate containing a low concentration of chelating agent is contacted with the gelled alginate, the citrate at the interface liquifies the surface of the alginate gel, which then mixes with the liquid alginate.

Subsequent use of gelling agent (in a second step) then gels the liquid alginate layer and the liquefied surface of the alginate gel, which has, at least in part, been mixed with the liquid alginate, thus forming a strong bond between the two layers as a result of formation of new crosslinks between the alginate gel of the previously gelled layer (e.g., the core) and the newly-formed alginate gel of the subsequent layer (e.g., the coat layer). In a similar fashion, alginate gel of the coat layer can be bonded to alginate gel of the overcoat layer.

The rapidity of the crosslinking reaction can be exploited to make a smooth surface on the implant. If the membrane surface of the mold 12 is wetted with a calcium (or other multivalent cation) solution at the moment of contact with liquid alginate, the rapid gelation reaction instantly produces a smooth surface.

The fabrication sequence begins with forming either the core or the two coat halves, then to forming the coated core, then optionally, to adding the overcoat.

A typical fabrication sequence is illustrated in FIGS. 4, 5 and 6. The frit 11 and membranes 12 of the molds are shown. Fabrication of the core is illustrated in FIG. 4. The optional core mesh 2 is surrounded by alginate 3 and islets 1. Note that some islets touch the membrane 6. The core is gelled by diffusing in a crosslinking agent (e.g., calcium ion) through the frit 11.

Fabrication of the coated core is illustrated in FIG. 5.

The core (1–3) is now surrounded by the coat 4. The liquid coat alginate 4, applied to the upper and lower surfaces of the core, containing a low concentration of citrate, mixes with the surface of the core alginate 3. Note that where an islet touched the membrane of the core mold 6, it is now safely within the coat. The coated core is gelled by diffusing in a crosslinking agent (e.g., calcium ion) through the frit 11.

The optional overcoat 5 is added as shown in FIG. 6. The final layer, whether it be the coat or overcoat, may be prepared by wetting the surface of an appropriate mold with a solution of crosslinking agent, and contacting the solution of crosslinking agent with the liquid alginate of the surface layer to make a smooth surface on the bioartificial implant.

Core mesh 2 may optionally be added to increase the strength of the implant. At higher concentrations of alginate, alginate gel is sufficiently strong that mesh may not be required. The mesh can be of any monofilament or multifilament natural or synthetic polymer. The multifilament fabric mesh shown in FIGS. 9, 10 and 11 has the further advantage of allowing alginate gel to penetrate the mesh fibers, increasing bonding of the core alginate 3 to the mesh 2.

The thickness of the implant and each of its layers is controlled by the mold dimensions. To produce an implant of 400 μm thickness, the core mold, for instance, may have a void depth of 300 μm. The coating mold may then have a void depth of 350 μm, and the overcoating mold a void depth of 400 μm.

The cellular or tissue implant of the present invention typically has a total volume of at least 10 cubic millimeters. Preferably, the total volume is at least 100 cubic millimeters and, more preferably, at least 500 cubic millimeters.

FIG. 3 illustrates an alternative method for fabricating the coated core. Here, the coat halves 4 have been fabricated in the mold illustrated in FIG. 8. Thereafter, the liquid core 1 and 3 and mesh 2 are added, and the molds pressed together. Bonding between the gelled coat halves 4 and the liquid core 3 proceeds as described above, followed by immersing the assembly in crosslinking agent (e.g., calcium ion solution) to effect complete gelation of the whole coated core.

FIG. 3 also illustrates the crucial regions near the edge of the mold where the core and the two mold halves come together. The dimensions of the implant and its component layers are controlled by mold dimensions by analogy with the description above.

An effect similar to that achieved with liquefying agent can be achieved by diffusing barium into the gel before the liquid alginate is brought into contact with the gelled alginate. The barium bound to the alginic acid is displaced by the monovalent cations of the liquid alginate and diffuses out of the gel into the liquid where it interacts with residues of the liquid alginate, thereby partially crosslinking the liquid alginate and partially liquefying the alginate gel. Subsequent exposure to chelating agent completes crosslinking of the two layers.

Another variation is to produce coating halves by schooling liquid alginate onto membranes, which can be peeled away from the newly fabricated coated core by wetting with liquefying agent.

Numerous other variations in the sequence of gelation, crosslinking and diffusion of gelling and liquefying agents exist, some of which are described in the Examples.

The present invention is further illustrated by the following specific but non-limiting examples. Percents are given in weight percents and temperature in degrees Centigrade unless otherwise specified. All solutions are aqueous unless otherwise indicated.

EXAMPLE 1

Na Alginate Solution Preparation

Briefly, a solution of Na alginate (LV Alginate/Kelco Division of Merck & Co.) was clarified by filtration and treated with activated charcoal (perchlorate bleached). The resulting solution was precipitated by adjusting the pH to 2 with HCl. The precipitate was redissolved in 120 mM NaCl-5 $\mu$M EDTA-10 mM HEPES solution and reprecipitated by addition of ethanol. The precipitate was partially redissolved in 1 M KCl, and the remaining insoluble fraction was dissolved in 120 mM NaCl-5 $\mu$M EDTA-10 mM HEPES solution and reprecipitated by addition of ethanol. The final precipitate was washed thoroughly with ethanol and dried in vacuo at 80° C.

To prepare alginate solutions of under 5% concentration, the resulting dry material was redissolved in 10 mM HEPES-10 mM Na citrate-110 mM NaCl, dialyzed (10 kD) against 10 mM HEPES-10 mM Na citrate-110 mM NaCl, and filtered through a 0.1 $\mu$m membrane.

To prepare alginate solutions of over 5% concentration, the resulting dry material was redissolved to a 1% solution, dialyzed (10 kD) against $H_2O$, then filtered through a 0.1 $\mu$m membrane. The alginate was sterilely lyophilized then redissolved to the desired concentration in sterile 10 mM HEPES-10 mM Na citrate-110 mM NaCl.

EXAMPLE 2

Islet Suspension Preparation

The preparation was performed under sterile conditions.

Islets isolated from rats were washed with isotonic NaCl and suspended in a 2% alginate solution (prepared by the procedure of Example 1) at a concentration of 150,000 islets per milliliter.

EXAMPLE 3

Bioartificial Implant Preparation by Molded Gum Coat Method

The preparation was performed under sterile conditions.

Using the coating mold, the two halves of the coat were prepared as follows. A thin plastic film was applied to the upper coating mold. A 20% Na alginate solution was prepared according to the method in Example 1, then a quantity sufficient to produce a 20 $\mu$m alginate half coat was applied to the lower mold. This material is considered a gum because, although liquid, it is viscous due to the high concentration of alginate. The two mold halves were pressed together. The upper mold was removed, and the thin plastic film carefully peeled off the coat half. The second coat half was prepared in the same way.

One half of the islet suspension described in Example 2 was placed on the prepared coat half remaining in the lower coating mold. A mesh (Allied Silicone, Ventura, Calif.) was cut to a size slightly smaller than the inner diameter of the mold (so as to fit within the depression in the prepared coat half reserved for the core). The remaining one half of the islet suspension was placed on the mesh in the lower coating mold. The total volume of mesh and suspension was chosen to exactly fill the void between the coat halves. The other lower coat mold was inverted and carefully pressed on to the first coating mold and clamped. Because both the core and coat alginates are liquid, they diffused into each other immediately. The assembly was immersed in a 120 mM $CaCl_2$-10 mM HEPES solution for 30 minutes to crosslink the alginate. The two mold halves were separated and the coated core removed.

The upper and lower overcoat molds were wetted with a solution of 120 mM $CaCl_2$-10 mM HEPES. A 2% solution of Na alginate was prepared by the method of Example 1 in a volume sufficient to form a 20 $\mu$m overcoat. One half of the Na alginate solution was placed in the overcoat mold. The coated core was washed with aqueous 120 mM NaCl-10 mM HEPES exhaustively, and was carefully placed in the overcoat mold. The second half of the Na alginate solution was placed in the overcoat mold. The upper overcoat mold was pressed onto the lower overcoat mold and clamped. The assembly was immersed in an aqueous 120 mM $CaCl_2$-10 mM HEPES solution for 30 minutes to crosslink the alginate. The two mold halves were separated and the overcoated coated core (complete bioartificial implant) removed.

EXAMPLE 4

Bioartificial Implant Preparation by Partial Coat Liquification

The preparation was performed under sterile conditions.

Using the coating mold, the two halves of the coat were prepared as follows. A 20% Na alginate solution was prepared according to the method in Example 1, then a quantity sufficient to produce a 20 $\mu$m alginate half coat was applied to each of the lower coat molds. The two upper molds were placed on the two lower molds, pressed together and clamped. The assembly was immersed in a 120 mM $CaCl_2$-10 mM HEPES solution for 30 minutes to crosslink the alginate.

The upper mold was removed and the coats washed exhaustively in place with 120 mM NaCl-10 mM HEPES. One half of the islet suspension described in Example 2 was placed on the prepared coat half remaining in the lower coating mold. A mesh (Allied Silicone, Ventura, Calif.) was cut to a size slightly smaller than the inner diameter of the mold (so as to fit within the depression in the prepared coat half reserved for the core). The remaining one half of the islet suspension was placed on the mesh in the lower coating mold. The total volume of mesh and suspension was chosen to exactly fill the void between the coat halves. The other lower coat mold was inverted and carefully pressed onto the first coating mold and clamped. After 5 minutes incubation to allow partial dissolution of the coat alginate gel by interaction with citrate in the islet alginate suspension, the assembly was immersed in a 120 mM $CaCl_2$-10 mM HEPES solution for 30 minutes to crosslink the alginate core and couple it to the coat. The two mold halves were separated and the coated core removed.

The upper and lower overcoat molds were wetted with a solution of 120 mM $CaCl_2$-10 mM HEPES. A 2% solution of Na alginate was prepared by the method of Example 1 with a volume sufficient to form a 20 $\mu$m overcoat. One half of the Na alginate solution was placed in the overcoat mold. The coated core was washed with 120 mM NaCl-10 maM HEPES exhaustively, and was carefully placed in the overcoat mold. The second half of the Na alginate solution was placed in the overcoat mold. The upper overcoat mold was pressed on to the lower overcoat mold and clamped. The assembly was immersed in a 120 mM $CaCl_2$-10 mM HEPES solution for 30 minutes to crosslink the alginate. The two mold halves were separated and the overcoated coated core (complete bioartificial implant) removed.

EXAMPLE 5

Bioartificial Implant Preparation by Partial Core-Coat Interface Liquification

The preparation was performed under sterile conditions.

Using the coating mold, the two halves of the coat were prepared as follows. A 20% Na alginate solution was prepared according to the method in Example 1, then a quantity sufficient to produce a 20 μm alginate half coat was applied to each of the lower coat molds. The two upper molds were placed on the two lower molds, pressed together and clamped. The assembly was immersed in a 120 mM $CaCl_2$-10 ml HEPES solution for 30 minutes to crosslink the alginate.

The upper mold was removed and the coats washed exhaustively in place with 120 mM NaCl-10 mM HEPES. One half of the islet suspension described in Example 2 was placed in the lower core mold. A mesh (Allied Silicone, Ventura, Calif.) was cut to slightly smaller than the inner diameter of the mold (so as to fit within the depression in the mold reserved for the core). The remaining one half of the islet suspension was placed on the mesh in the lower core mold. The total volume of mesh and suspension was chosen to exactly fill the void between the coat halves. The two molds were pressed together and clamped. The assembly was immersed in a 120 mM $CaCl_2$-10 mM HEPES solution for 30 minutes to crosslink the alginate.

The upper and lower core mold were separated and the core removed. A few drops of 1.5% Na alginate-10 mM Na citrate-10 mM HEPES-110 mM NaCl were applied to the center of one of the coating halves in its coating mold half. The core was placed on top and a few drops of 1.5% Na alginate-10 mM Na citrate-10 mM HEPES-110 mM NaCl were applied to the top of the core. The other coat half in its coating mold half was pressed down on top and the entire assembly clamped. The assembly was immersed in a 120 mM $CaCl_2$-10 mM HEPES solution for 30 minutes to couple the alginate core to the coat. The two mold halves were separated and the coated core removed.

The upper and lower overcoat molds were wetted with a solution of 120 mM $CaCl_2$-10 mM HEPES. A 2% solution of Na alginate was prepared by the method of Example 1 with a volume sufficient to form a 20 μm overcoat. One half of the Na alginate solution was placed in the overcoat mold. The coated core was washed with 120 mM NaCl-10 mM HEPES exhaustively, and was carefully placed in the overcoat mold. The second half of the Na alginate solution was placed in the overcoat mold. The upper overcoat mold was pressed on to the lower overcoat mold and clamped. The assembly was immersed in a 120 mM $CaCl_2$-10 mM HEPES solution for 30 minutes to crosslink the alginate. The two mold halves were separated and the overcoated coated core (complete bioartificial implant) removed.

EXAMPLE 6

Bioartificial Implant Preparation by Diffusion Coat Method

The preparation was performed under sterile conditions.

One half of the islet suspension described in Example 2 was placed in the lower core mold. A mesh (Allied Silicone, Ventura, Calif.) was cut to slightly smaller than the inner diameter of the mold (so as to fit within the depression in the mold reserved for the core). The remaining one half of the islet suspension was placed on the mesh in the lower core mold. The total volume of mesh and suspension was chosen to exactly fill the void between the coat halves. The two molds were pressed together and clamped. The assembly was immersed in a 120 mM $CaCl_2$ 10 mM HEPES solution for 30 minutes to crosslink the alginate.

The upper and lower core mold were separated and the core removed and immersed in 120 mM $BaCl_2$-10 mM HEPES for 5 minutes to effect an exchange reaction between Ca and Ba ions. The core was then washed exhaustively with 120 mM NaCl.

A solution of 20% Na alginate prepared by the method of Example 1 of sufficient volume to product a 20 μm coat was prepared and half of the volume applied to the lower coat mold. The core was placed on top, overlaid with the remaining alginate solution, and incubated for 5 minutes to allow sodium in the coat alginate solution to exchange with barium bound to the core alginate and for liberated barium to diffuse into the coat alginate and crosslink it. The assembly was then immersed in a 120 mM $CaCl_2$-10 mM HEPES solution for 30 minutes to crosslink the alginate. The two mold halves were separated and the coated core removed.

The upper and lower overcoat molds were wetted with a solution of 120 mM CaCl-10 mM HEPES. A 2% solution of Na alginate was prepared by the method of Example 1 with a volume sufficient to form a 20 μm overcoat. One half of the Na alginate solution was placed in the overcoat mold. The coated core was washed with 120 mM NaCl-10 mM HEPES exhaustively, and was carefully placed in the overcoat mold. The second half of the Na alginate solution was placed in the overcoat mold. The upper overcoat mold was pressed on to the lower overcoat mold and clamped. The assembly was immersed in a 120 mM $CaCl_2$-10 mM HEPES solution for 30 minutes to crosslink the alginate. The two mold halves were separated and the overcoated coated core (complete bioartificial implant) removed.

EXAMPLE 7

Pancreatic Islet Implant into Diabetic Mice (IP)

Host Balb/C mice were rendered diabetic by IP injection of 250 mg/kg of streptozotocin at 50 mg/ml in 0.1 M citrate buffer, pH=4.5, several days prior to implantation. Bioartificial implants prepared according to Example 4 containing 2000–3000 islets were inserted into the peritoneal cavity through an abdominal incision and the mice were sutured.

What is claimed as new and is desired to be secured by Letters Patent of the United States is:

1. A viable, physiologically active and biocompatible cellular or tissue implant having (a) a total volume greater than 10 cubic millimeters, (b) a tissue or cell content of at least 10% by volume, and (c) dimensions permitting sufficient oxygen diffusion to sustain cell or tissue viability when the implant is implanted into a vascularized site in a patient.

2. The implant of claim 1, wherein said total volume is at least 100 cubic millimeters.

3. The implant of claim 1, wherein said total volume is at least 500 cubic millimeters.

4. The implant of claim 1, wherein said tissue or cell content is at least 20% by volume.

5. The implant of claim 2, wherein said tissue or cell content is at least 35% by volume.

6. The implant of claim 1, wherein the implant has a thin sheet configuration.

7. The implant of claim 1, wherein the implant has a thickness of less than 400 μm.

8. The implant of claim 1, wherein the implant is retrievable.

9. The implant of claim 1, wherein the implant comprises (a) a core of living tissue and a first gelled alginate, surrounded by (b) one or more layers of a second gelled alginate, which may be the same as or different from said first gelled alginate.

10. The implant of claim 9, wherein said core further comprises one or more trophic factors or nurse cells.

11. The implant of claim 9, wherein said core further comprises a substrate material.

12. The implant of claim 9, where said core further comprises an antioxidant material.

13. The implant of claim 9, wherein said living tissue comprises islets of Langerhans.

14. A method of treating or preventing a disease which can be treated or prevented with an active agent secreted by a cell or tissue, comprising implanting the implant of claim 1 in a patient in need thereof.

15. A method of treating or preventing a disease which can be treated or prevented by catabolism of a disease-causing agent or substance in a cell or tissue, comprising implanting the implant of claim 1 in a patient in need thereof.

16. The method of claim 14, wherein said disease is diabetes.

17. The implant of claim 9, wherein said core further comprises trophic factors and nurse cells.

* * * * *